United States Patent [19]
Grandy et al.

[11] Patent Number: 5,837,809
[45] Date of Patent: Nov. 17, 1998

[54] MAMMALIAN OPIOID RECEPTOR LIGAND AND USES

[75] Inventors: David K. Grandy; James R. Bunzow, both of Portland, Oreg.; Olivier Civelli, Aesch, Switzerland; Rainer Klaus Reinscheid, Eimeldingen; Hans-Peter Nothacker, Schliengen, both of Germany; Frederick James Monsma, Riehen, Switzerland

[73] Assignee: Oregon Health Sciences University, Portland, Oreg.

[21] Appl. No.: 514,451

[22] Filed: Aug. 11, 1995

[51] Int. Cl.$^6$ .......................... C07K 7/08; C07K 14/705
[52] U.S. Cl. ..................... 530/326; 530/300; 530/350; 435/69.1
[58] Field of Search .................... 530/300, 350, 530/326; 514/2, 12; 435/69.1

[56] References Cited

PUBLICATIONS

Zagon et al., Neuroscience Research, 3, 1–19, 1985.
Reinscheid et al., Science, 270, 792–794, 1995.
Meunier et al., Nature, 377, 532–535, 1995.
Saito et al., Biochem. and Biophys. Res. Commun., 217, 539–545, 1995.

*Primary Examiner*—Sally P. Teng
*Attorney, Agent, or Firm*—Klarquist Sparkman Campbell Leigh & Whinston, LLP

[57] ABSTRACT

The present invention relates to a novel mammalian opioid receptor protein and ligands that bind to such proteins. The invention is directed toward the isolation, characterization and pharmacological use of an endogenous ligand that specifically binds to a novel mammalian opioid receptor protein heterologously expressed in mammalian cells. The invention specifically provides the isolated peptide ligand and analogues, derivatives and variants thereof. The invention specifically provides tyrosine substitution variants of the peptide ligand that specifically bind to the opioid receptor and can be radioiodinated. Also provided are methods of making such peptide ligands and methods of using the ligands for diagnostic and therapeutic uses and for the identification of other naturally-occurring or synthetic opioid receptor ligands.

4 Claims, 11 Drawing Sheets

FIG. 1A

```
GTTCCTGTGTTGCCATCATGGGTTCAGCACAAGTGGAAGATGAAGAGATCGAGTGCCTGGTGGAGATCCCTGCC    790
       V P V A I M G S A Q V  E D E E I E C  L V E I P A

CCTCAGGACTATTGGGGCCCCTGTATTCGCCCTCTTCCTCATCTGCCATCTTCTTTTTCCTCATCATCCCTGTGCTGATC    862
 P Q D Y W G P P V F A  I C I F L F S F I I P V L I
                                                                       V

ATCTCTGTCTGCTACAGCCTCATGATTCGACGACTCGTGGTCCGTCTGCTCTTCAGGCTCCGGGAGAAG    934
 I S V C Y S L M I R  R  L R G V R L L S G S R E K

GACCGAAACCTGCGGCGTATCACTCGACTGGTGCTGGTGGTGGTGGTGGCTGTGTTTGTGGGGCTGGACGCCT    1006
 D R N L R R I T R  L V L V V V A V F V G C W T P
                                              VI

GTGCAGGTGTTGTCCTGGTTCAAGGACTGGGTTCAGCAGGTGTTCAGCCAGGTAGTGAGACTGCCATCCTGCGC    1078
 V Q F V L  V Q G L G V Q P P G S E T A V A I L R

TTCTGCACAGCCCTGGGCTATGTCAACAGTGTCTGCAATCCCATTCTCTATGCTTTCCTGGATGAGAACTTC    1150
 F C T A L G Y V N S C L N P I L Y A F L D D E N F
                         VII

AAGGCCTGCTTTAGAAAGTTCTGCTGTGCTTCATCCCTGCACCGGGAGATGCAGGTTTCTGATCGTGTGCGG    1222
 K A C F R K F C C A S S L H R E M Q V S D R V R
                                                  *

GCGATTGCCAAGGATGTTGGCCTTGGCTGCAAGACTTCTGAGACAGTACCACGGCCAGCATGACTAGGCGTG    1294
 S I A K D V G L G C K T S E T V P R P A

GACCTGCCCATGGTGCCCTGTCAGCCCACAGAGCCCATCCTACACCCAACAGGAGCTCACACAGGTCACTGC    1366
TCTCTAGGTTGACCCTGAACCTTGAGCATCTGGAGCCCTTGAATGGCTTTTCTTTTGATCAGGATGCTCAGT    1438
CCTAGAGGAAGACC
```

FIG. 1B

Amino acid alignment

```
LC132                                         MESLFPAPYWEVL
Rat μ-Opioid Receptor    MDSSTGPGNTSDCSDPLAQASCSPAPGSWLNLS
Mouse δ-Opioid Receptor                       MELVPSARAELQSS
Mouse κ-Opioid Receptor             MESPIQIFRGDPGPTCSPSACLLP
```

I
```
LC132  YGSHFQGNLSLLNETVPHHLLLNASHSAFLPLGLKVTIVGLYLAVCIGGLLGNCL
μ-OR   HVDGNQSDPCGLNRTGLGGNDSLCPQTGSPSMVTAITIMALYSIVCVVGLFGNFL
δ-OR   PLVNLSDAFPSAFPSAGANASGSPGARSASSLALAIAITALYSAVCAVGLLGNVL
κ-OR   NSSSWFPNWAESDSNGSVGSEDQQLESAHISPAIPVIITAVYSVVFVVGLVGNSL
```

II
```
LC132  VMYVILRHTKMKTATNIYIFNLALADTLVLLTLPFQGTDILLGFWPFGNALCKTV
μ-OR   VMYVIVRYTKMKTATNIYIFNLALADALATSTLPFQSVNYLMGTWPFGTILCKIV
δ-OR   VMFGIVRYTKLFTATNIYIFNLALADALATSTLPFQSAKYLMETWPFGELLCKAV
κ-OR   VMFVIIRYTKMKTATNIYIFNLALADALVTTMPFQSAVYLMNSWPFGDVLCKIV
```

III                                      IV
```
LC132  IAIDYYNMFTSTFFTLTAMSVDRYVAICHPIRALDVRTSSKAQAVNVAIWALASVV
μ-OR   ISIDYYNMFTSIFTLCTMSVDRYIAVCHPVKALDFRTPRNAKIVNVCNWILSSAI
δ-OR   LSIDYYNMFTSIFTLTMMSVDRYIAVCHPVKALDFRTPAKAKLINICIWVLASGV
κ-OR   ISIDYYNMFTSIFTLTMMSVDRYIAVCHPVKALDFRTPLKAKIINICIWLLASSV
```

FIG. 2A

```
                       V
LC132  GVPVAIMGSAQ   VEDEEIECLVEIPAP QDYWGPVFA ICIFLFSFIIPVLIISV
μ-OR   GLPVMFMATTK   YRQGSIDCTLTFSHP TWYWENLLK ICVFIFAFIMPILIITV
δ-OR   GVPIMVMAVTQ   PRDFAVVCMLQFPSP SWYWDTVTK ICVFLFAFVVPILIITV
κ-OR   GISAIVLGGTKVREDVDVIECSLQFPDDEYSWWDLFMK ICVFVFAFVIPVLIIIV

VI
LC132  CYSLMIRRLRGVRLLSGSREKDRNLRRITRLVLVVV AVFVGCWTPVQVFVLVQGL
μ-OR   CYGLMILRLRSVRMLSGSKEKDRNLRRITRMVLVVV AVFIVCWTPIHIYVIIKAL
δ-OR   CYGLMLLRLRSVRLLSGSKEKDRSLRRITRMVLVVV GAFVVCWAPIHIFVIVWTL
κ-OR   CYTLMILRLKSVRLLSGSREKDRNLRRITKLVLVVV AVFIICWTPIHIFILVEAL

VII
LC132  GVQPGSETAVAIL RFCTALGYVNSCLNPILYAFLDENFKACFRKFCCASSLHRE
μ-OR   ITIPETFFQTVSW HFCIALGYTNSCLNPVLYAFLDENFKRCFREFCIPTSSTIE
δ-OR   VDINRRDPLVVAALHLCIALGYANSSLNPVLYAFLDENFKRCFRQLCRTPCGRQE
κ-OR   GSTSHSTAALSSY YFCIALGYTNSSLNPVLYAFLDENFKRCFRDFCFPIKMRME

LC132  MQVSDRVRSIAKDVGLGCKTSETVPRPA     367
μ-OR   QQNSTRVRQNTREHPSTANTVDRTNHQLENLEAETAPLP 398
δ-OR   PGSLRRPRQATTRERVTACTPSDGPGGGAAA 372
κ-OR   RQSTNRVRNTVQDPASMRDVGGMNKPV      380
```

FIG. 2B

3H-METHADONE BINDING TO COS-7 MEMBRANES

3H-METHADONE BINDING TO LC132 IN COS-7 MEMBRANES

FIG. 7

Tyr-Gly-Gly-Phe-Thr-Gly-Ala-Arg-Lys-Ser-Ala-Arg-Lys-Leu-Ala-Asn-Gln        Orphanin FQ
Tyr-Gly-Gly-Phe-Leu-Arg-Arg-Ile-Arg-Pro-Lys-Leu-Lys-Trp-Asp-Asn-Gln        Dynorphin A
Tyr-Gly-Gly-Phe-Met-Thr-Ser-Glu-Lys-Ser-Gln-Thr-Pro-Leu-Val-Thr            α-Endorphin
Tyr-Gly-Gly-Phe-Leu-Arg-Arg-Gln-Phe-Lys-Val-Val-Thr                         Dynorphin B
Tyr-Gly-Gly-Phe-Leu                                                         Leu-Enkephalin

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE:
        ( A ) DESCRIPTION: DNA (genomic)

( x i ) SEQUENCE DESCRIPTION: SEQ ID NO:1:

ATGAATTCAC NRTSATGAGY GTSGACHGHT A         3 1

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE:
        ( A ) DESCRIPTION: DNA (genomic)

( x i ) SEQUENCE DESCRIPTION: SEQ ID NO:2:

TTGTCGACRT ARRAGRAYNG GRTT         2 4

( 2 ) INFORMATION FOR SEQ ID NO:3:

( i ) SEQUENCE CHARACTERISTICS:
        ( A ) LENGTH: 1452 base pairs
        ( B ) TYPE: nucleic acid
        ( C ) STRANDEDNESS: single
        ( D ) TOPOLOGY: linear ( i i ) MOLECULE TYPE:
        ( A ) DESCRIPTION: cDNA ( i x ) FEATURE:
        ( A ) NAME/KEY: 5'UTR
        ( B ) LOCATION: 1..181

( i x ) FEATURE:

( A ) NAME/KEY: CDS
( B ) LOCATION: 182..1282

( i x ) FEATURE:
( A ) NAME/KEY: 3'UTR
( B ) LOCATION: 1283..1452

( x i ) SEQUENCE DESCRIPTION: SEQ ID NO:3:

| | | | | | |
|---|---|---|---|---|---|
| CCGAGGAGCC | ATTCCCAGCC | GCAGCAGACC | CCAATCTAGA | GTGAGAGTCA | TTGCTCAGTC | 60 |
| CACTGTGCTC | CTGCCTGCCC | GCCTTTCTGC | TAAGCATTGG | GGTCTATTTT | GCGCCCAGCT | 120 |
| TCTGAAGAGG | CTGTGTGTGC | CGTTGGAGGA | ACTGTACTGA | GTGGCTTTGC | AGGGTGACAG | 180 |

```
C  ATG  GAG  TCC  CTC  TTT  CCT  GCT  CCA  TAC  TGG  GAG  GTC  TTG  CAT  GGC         226
   Met  Glu  Ser  Leu  Phe  Pro  Ala  Pro  Tyr  Trp  Glu  Val  Leu  His  Gly
   1                 5                        10                      15

AGC  CAC  TTT  CAA  GGG  AAC  CTG  TCC  CTC  CTA  AAT  GAG  ACC  GTA  CCC  CAC    274
Ser  His  Phe  Gln  Gly  Asn  Leu  Ser  Leu  Leu  Asn  Glu  Thr  Val  Pro  His
20                  25                       30

CAC  CTG  CTC  CTC  AAT  GCT  AGT  CAC  AGC  GCC  TTC  CTG  CCC  CTT  GGA  CTC    322
His  Leu  Leu  Leu  Asn  Ala  Ser  His  Ser  Ala  Phe  Leu  Pro  Leu  Gly  Leu
        35                       40                       45

AAG  GTC  ACC  ATC  GTG  GGG  CTC  ATC  TTG  GCT  GTG  TGC  ATC  GGG  GGG  CTC    370
Lys  Val  Thr  Ile  Val  Gly  Leu  Ile  Leu  Ala  Val  Cys  Ile  Gly  Gly  Leu
50                       55                       60

CTG  GGG  AAC  TGC  CTC  GTC  ATG  TAT  GTC  ATC  CTC  AGG  ACA  CCC  AAG  ATG    418
Leu  Gly  Asn  Cys  Leu  Val  Met  Tyr  Val  Ile  Leu  Arg  Thr  Pro  Lys  Met
        65                       70                       75

AAG  ACA  GCT  ACC  AAC  ATT  TAC  ATA  TTT  AAT  CTG  GCA  CTG  GCT  GAT  ACC    466
Lys  Thr  Ala  Thr  Asn  Ile  Tyr  Ile  Phe  Asn  Leu  Ala  Leu  Ala  Asp  Thr
80                       85                       90                       95

CTG  GTC  TTG  CTA  ACA  CTG  CCC  TTC  CAG  GGC  ACA  GAC  ATC  CTA  CTG  GGC    514
Leu  Val  Leu  Leu  Thr  Leu  Pro  Phe  Gln  Gly  Thr  Asp  Ile  Leu  Leu  Gly
100                      105                      110

TTC  TGG  CCA  TTT  GGG  AAA  GCA  CTC  TGC  AAG  ACT  GTC  ATT  GCT  ATC  GAC    562
Phe  Trp  Pro  Phe  Gly  Lys  Ala  Leu  Cys  Lys  Thr  Val  Ile  Ala  Ile  Asp
        115                      120                      125

TAC  TAC  AAC  ATG  TTT  ACC  AGC  ACT  TTT  ACT  CTG  ACC  GCC  ATG  AGC  GTA    610
Tyr  Tyr  Asn  Met  Phe  Thr  Ser  Thr  Phe  Thr  Leu  Thr  Ala  Met  Ser  Val
130                      135                      140

GAC  CGC  TAT  GTG  GCT  ATC  TGC  CAC  CCT  ATC  CGT  GCC  CTT  GAT  GTT  CGG    658
Asp  Arg  Tyr  Val  Ala  Ile  Cys  His  Pro  Ile  Arg  Ala  Leu  Asp  Val  Arg
        145                      150                      155

ACA  TCC  AGC  AAA  GCC  CAG  GCT  GTT  AAT  GTG  GCC  ATA  TGG  GCC  CTG  GCT    706
Thr  Ser  Ser  Lys  Ala  Gln  Ala  Val  Asn  Val  Ala  Ile  Trp  Ala  Leu  Ala
160                      165                      170                      175

TCA  GTG  GTT  GGT  GTT  CCT  GTT  GCC  ATC  ATG  GGT  TCA  GCA  CAA  GTG  GAA    754
Ser  Val  Val  Gly  Val  Pro  Val  Ala  Ile  Met  Gly  Ser  Ala  Gln  Val  Glu
        180                      185                      190

GAT  GAA  GAG  ATC  GAG  TGC  CTG  GTG  GAG  ATC  CCT  GCC  CCT  CAG  GAC  TAT    802
Asp  Glu  Glu  Ile  Glu  Cys  Leu  Val  Glu  Ile  Pro  Ala  Pro  Gln  Asp  Tyr
        195                      200                      205

TGG  GGC  CCT  GTA  TTC  GCC  ATC  TGC  ATC  TTC  CTT  TTT  TCC  TTC  ATC  ATC    850
Trp  Gly  Pro  Val  Phe  Ala  Ile  Cys  Ile  Phe  Leu  Phe  Ser  Phe  Ile  Ile
210                      215                      220

CCT  GTG  CTG  ATC  ATC  TCT  GTC  TGC  TAC  AGC  CTC  ATG  ATT  CGA  CGA  CTT    898
Pro  Val  Leu  Ile  Ile  Ser  Val  Cys  Tyr  Ser  Leu  Met  Ile  Arg  Arg  Leu
        225                      230                      235

CGT  GGT  GTC  CGT  CTG  CTT  TCA  GGC  TCC  CGG  GAG  AAG  GAC  CGA  AAC  CTG    946
Arg  Gly  Val  Arg  Leu  Leu  Ser  Gly  Ser  Arg  Glu  Lys  Asp  Arg  Asn  Leu
240                      245                      250                      255

CGG  CGT  ATC  ACT  CGA  CTG  GTG  CTG  GTA  GTG  GTG  GCT  GTG  TTT  GTG  GGC    994
```

| | | | | | | | | | | | | | | |
|---|---|---|---|---|---|---|---|---|---|---|---|---|---|---|
| Arg | Arg | Ile | Thr | Arg | Leu | Val | Leu | Val | Val | Val | Ala | Val | Phe | Val | Gly |
| 260 | | | | 265 | | | | | 270 | | | | | | |

```
TGC TGG ACG CCT GTG CAG GTG TTT GTC CTG GTT CAA GGA CTG GGT GTT     1042
Cys Trp Thr Pro Val Gln Val Phe Val Leu Val Gln Gly Leu Gly Val
    275                 280                 285

CAG CCA GGT AGT GAG ACT GCA GTT GCC ATC CTG CGC TTC TGC ACA GCC     1090
Gln Pro Gly Ser Glu Thr Ala Val Ala Ile Leu Arg Phe Cys Thr Ala
290                 295                 300

CTG GGC TAT GTC AAC AGT TGT CTC AAT CCC ATT CTC TAT GCT TTC CTG     1138
Leu Gly Tyr Val Asn Ser Cys Leu Asn Pro Ile Leu Tyr Ala Phe Leu
    305                 310                 315

GAT GAG AAC TTC AAG GCC TGC TTT AGA AAG TTC TGC TGT GCT TCA TCC     1186
Asp Glu Asn Phe Lys Ala Cys Phe Arg Lys Phe Cys Cys Ala Ser Ser
320                 325                 330                 335

CTG CAC CGG GAG ATG CAG GTT TCT GAT CGT GTG CGG ACG ATT GCC AAG     1234
Leu His Arg Glu Met Gln Val Ser Asp Arg Val Arg Thr Ile Ala Lys
    340                 345                 350

GAT GTT GGC CTT GGT TGC AAG ACT TCT GAG ACA GTA CCA CGG CCA GCA     1282
Asp Val Gly Leu Gly Cys Lys Thr Ser Glu Thr Val Pro Arg Pro Ala
355                 360                 365

TGACTAGGCG TGGACCTGCC CATGGTGCCT GTCAGCCCAC AGAGCCCATC CTACACCCAA   1342

CACGGAGCTC ACACAGGTCA CTGCTCTCTA GGTTGACCCT GAACCTTGAG CATCTGGAGC   1402

CTTGAATGGC TTTTCTTTTG GATCAGGATG CTCAGTCCTA GAGGAAGACC              1452
```

( 2 ) INFORMATION FOR SEQ ID NO:4:

( i ) SEQUENCE CHARACTERISTICS:
        ( A ) LENGTH: 367 amino acids
        ( B ) TYPE: amino acid
        ( D ) TOPOLOGY: linear ( i i ) MOLECULE TYPE:
        ( A ) DESCRIPTION: protein ( x i ) SEQUENCE DESCRIPTION: SEQ ID NO:4:

```
Met Glu Ser Leu Phe Pro Ala Pro Tyr Trp Glu Val Leu His Gly Ser
                1               5                   10

His Phe Gln Gly Asn Leu Ser Leu Leu Asn Glu Thr Val Pro His His
            20                  25                  30

Leu Leu Leu Asn Ala Ser His Ser Ala Phe Leu Pro Leu Gly Leu Lys
        35                  40                  45

Val Thr Ile Val Gly Leu Ile Leu Ala Val Cys Ile Gly Gly Leu Leu
    50                  55                  60

Gly Asn Cys Leu Val Met Tyr Val Ile Leu Arg Thr Pro Lys Met Lys
65                  70                  75                  80

Thr Ala Thr Asn Ile Tyr Ile Phe Asn Leu Ala Leu Ala Asp Thr Leu
                85                  90                  95

Val Leu Leu Thr Leu Pro Phe Gln Gly Thr Asp Ile Leu Leu Gly Phe
            100                 105                 110

Trp Pro Phe Gly Lys Ala Leu Cys Lys Thr Val Ile Ala Ile Asp Tyr
        115                 120                 125

Tyr Asn Met Phe Thr Ser Thr Phe Thr Leu Thr Ala Met Ser Val Asp
    130                 135                 140

Arg Tyr Val Ala Ile Cys His Pro Ile Arg Ala Leu Asp Val Arg Thr
145                 150                 155                 160

Ser Ser Lys Ala Gln Ala Val Asn Val Ala Ile Trp Ala Leu Ala Ser
                165                 170                 175

Val Val Gly Val Pro Val Ala Ile Met Gly Ser Ala Gln Val Glu Asp
```

```
                           180                      185                        190
Glu  Glu  Ile  Glu  Cys  Leu  Val  Glu  Ile  Pro  Ala  Pro  Gln  Asp  Tyr  Trp
               195                      200                      205
Gly  Pro  Val  Phe  Ala  Ile  Cys  Ile  Phe  Leu  Phe  Ser  Phe  Ile  Ile  Pro
     210                      215                      220
Val  Leu  Ile  Ile  Ser  Val  Cys  Tyr  Ser  Leu  Met  Ile  Arg  Arg  Leu  Arg
225                      230                      235                          240
Gly  Val  Arg  Leu  Leu  Ser  Gly  Ser  Arg  Glu  Lys  Asp  Arg  Asn  Leu  Arg
                    245                      250                          255
Arg  Ile  Thr  Arg  Leu  Val  Leu  Val  Val  Ala  Val  Phe  Val  Gly  Cys
               260                      265                      270
Trp  Thr  Pro  Val  Gln  Val  Phe  Val  Leu  Val  Gln  Gly  Leu  Gly  Val  Gln
               275                      280                      285
Pro  Gly  Ser  Glu  Thr  Ala  Val  Ala  Ile  Leu  Arg  Phe  Cys  Thr  Ala  Leu
          290                      295                      300
Gly  Tyr  Val  Asn  Ser  Cys  Leu  Asn  Pro  Ile  Leu  Tyr  Ala  Phe  Leu  Asp
305                           310                      315                     320
Glu  Asn  Phe  Lys  Ala  Cys  Phe  Arg  Lys  Phe  Cys  Cys  Ala  Ser  Ser  Leu
                    325                      330                          335
His  Arg  Glu  Met  Gln  Val  Ser  Asp  Arg  Val  Arg  Thr  Ile  Ala  Lys  Asp
               340                      345                      350
Val  Gly  Leu  Gly  Cys  Lys  Thr  Ser  Glu  Thr  Val  Pro  Arg  Pro  Ala
               355                      360                 365
```

( 2 ) INFORMATION FOR SEQ ID NO: 5:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE:
        ( A ) DESCRIPTION: peptide ( x i ) SEQUENCE DESCRIPTION: SEQ ID NO:5:

```
Phe  Gly  Gly  Phe  Thr  Gly  Ala  Arg  Lys  Ser  Ala  Arg  Lys  Leu  Ala  Asn
 1                   5                        10                           15
Gln
```

( 2 ) INFORMATION FOR SEQ ID NO: 6:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE:
        ( A ) DESCRIPTION: peptide ( x i ) SEQUENCE DESCRIPTION: SEQ ID NO:6:

```
Phe  Gly  Gly  Phe  Thr  Gly  Ala  Arg  Lys  Ser  Ala  Arg  Lys  Tyr  Ala  Asn
 1                   5                        10                           15
Gln
```

( 2 ) INFORMATION FOR SEQ ID NO: 7:

( i ) SEQUENCE CHARACTERISTICS:
        ( A ) LENGTH: 367 amino acids
        ( B ) TYPE: amino acid
        ( C ) TOPOLOGY: linear ( i i ) MOLECULE TYPE:

(A) DESCRIPTION: peptide (xi) SEQUENCE DESCRIPTION: SEQ ID NO:7:

| Met | Glu | Ser | Leu | Phe | Pro | Ala | Pro | Tyr | Trp | Glu | Val | Leu | His | Gly | Ser |
|---|---|---|---|---|---|---|---|---|---|---|---|---|---|---|---|
| 1 | | | | 5 | | | | | 10 | | | | | 15 | |
| His | Phe | Gln | Gly | Asn | Leu | Ser | Leu | Leu | Asn | Glu | Thr | Val | Pro | His | His |
| | | | 20 | | | | | 25 | | | | | 30 | | |
| Leu | Leu | Leu | Asn | Ala | Ser | His | Ser | Ala | Phe | Leu | Pro | Ser | Gly | Leu | Lys |
| | | 35 | | | | | 40 | | | | | 45 | | | |
| Val | Thr | Ile | Val | Gly | Leu | Ile | Leu | Ala | Val | Cys | Ile | Gly | Gly | Leu | Leu |
| | 50 | | | | | 55 | | | | | 60 | | | | |
| Gly | Met | Cys | Leu | Val | Met | Tyr | Val | Ile | Leu | Arg | Thr | Pro | Lys | Met | Lys |
| 65 | | | | | 70 | | | | | 75 | | | | | 80 |
| Thr | Ala | Thr | Asn | Ile | Tyr | Ile | Phe | Asn | Leu | Ala | Leu | Ala | Asp | Thr | Leu |
| | | | | 85 | | | | | 90 | | | | | 95 | |
| Val | Leu | Leu | Thr | Leu | Pro | Phe | Gln | Gly | Thr | Asp | Ile | Leu | Leu | Gly | Phe |
| | | | 100 | | | | | 105 | | | | | 110 | | |
| Trp | Pro | Phe | Gly | Lys | Ala | Leu | Cys | Lys | Thr | Val | Ile | Ala | Ile | Asp | Tyr |
| | | 115 | | | | | 120 | | | | | 125 | | | |
| Tyr | Lys | Met | Phe | Thr | Ser | Thr | Phe | Thr | Leu | Thr | Ala | Met | Ser | Val | Asp |
| | 130 | | | | | 135 | | | | | 140 | | | | |
| Arg | Tyr | Val | Ala | Ile | Cys | His | Pro | Ile | Arg | Ala | Leu | Asp | Val | Arg | Thr |
| 145 | | | | | 150 | | | | | 155 | | | | | 160 |
| Ser | Ser | Lys | Ala | Gln | Ala | Val | Met | Val | Ala | Ile | Trp | Ala | Leu | Ala | Ser |
| | | | | 165 | | | | | 170 | | | | | 175 | |
| Val | Val | Gly | Val | Pro | Val | Ala | Ile | Met | Gly | Ser | Ala | Gln | Val | Glu | Asp |
| | | | 180 | | | | | 185 | | | | | 190 | | |
| Glu | Glu | Ile | Glu | Cys | Leu | Val | Glu | Ile | Pro | Ala | Pro | Gln | Asp | Tyr | Trp |
| | | 195 | | | | | 200 | | | | | 205 | | | |
| Gly | Pro | Val | Phe | Ala | Ile | Cys | Ile | Phe | Leu | Phe | Ser | Phe | Ile | Ile | Pro |
| | 210 | | | | | 215 | | | | | 220 | | | | |
| Val | Leu | Ile | Ile | Ser | Val | Cys | Tyr | Ser | Leu | Met | Ile | Arg | Arg | Leu | Arg |
| 225 | | | | | 230 | | | | | 235 | | | | | 240 |
| Gly | Val | Arg | Leu | Leu | Ser | Gly | Ser | Arg | Lys | Lys | Asp | Arg | Asn | Leu | Arg |
| | | | | 245 | | | | | 250 | | | | | 255 | |
| Arg | Ile | Thr | Arg | Leu | Val | Leu | Val | Val | Ala | Val | Thr | Val | Gly | Cys |
| | | | 260 | | | | | 265 | | | | | 270 | | |
| Trp | Thr | Pro | Val | Ala | Val | Phe | Val | Leu | Val | Gln | Gly | Leu | Gly | Val | Gln |
| | | 275 | | | | | 280 | | | | | 285 | | | |
| Pro | Gly | Ser | Glu | Thr | Ala | Val | Ala | Ile | Leu | Arg | Phe | Cys | Thr | Ala | Leu |
| | 290 | | | | | 295 | | | | | 300 | | | | |
| Gly | Tyr | Val | Met | Ser | Cys | Leu | Met | Pro | Ile | Leu | Tyr | Ala | Phe | Leu | Asp |
| 305 | | | | | 310 | | | | | 315 | | | | | 320 |
| Lys | Met | Thr | Lys | Ala | Cys | Thr | Arg | Lys | Phe | Cys | Cys | Ala | Ser | Ser | Leu |
| | | | | 325 | | | | | 330 | | | | | 335 | |
| His | Arg | Glu | Met | Gln | Val | Ser | Asp | Arg | Val | Arg | Thr | Ile | Ala | Lys | Asp |
| | | | 340 | | | | | 345 | | | | | 350 | | |
| Val | Gly | Leu | Gly | Cys | Lys | Thr | Ser | Glu | Thr | Val | Pro | Arg | Pro | Ala | |
| | | 355 | | | | | 360 | | | | | 365 | | | |

(2) INFORMATION FOR SEQ ID NO:8:

(i) SEQUENCE CHARACTERISTICS:
(A) LENGTH: 398 amino acids
(B) TYPE: amino acid
(C) TOPOLOGY: linear (ii) MOLECULE TYPE:
    (A) DESCRIPTION: peptide (xi) SEQUENCE DESCRIPTION: SEQ ID NO:8:

```
Met Asp Ser Ser Thr Gly Pro Gly Asn Thr Ser Asp Cys Ser Asp Pro
 1               5                  10                  15

Leu Ala Gln Ala Ser Cys Ser Pro Ala Pro Gly Ser Trp Leu Asn Leu
                20                  25                  30

Ser His Val Asp Gly Asn Gln Ser Asp Pro Cys Gly Leu Asn Arg Thr
            35                  40                  45

Gly Leu Ala Gly Asn Asp Ser Leu Cys Pro Gln Thr Gly Ser Pro Ser
        50                  55                  60

Met Val Thr Ala Ile Thr Ile Met Ala Leu Tyr Ser Ile Val Cys Val
65                      70                  75                  80

Val Gly Leu Phe Gly Met Phe Leu Val Met Tyr Val Ile Val Arg Tyr
                85                  90                  95

Thr Lys Met Lys Thr Ala Thr Asn Ile Tyr Ile Phe Asn Leu Ala Leu
                100                 105                 110

Ala Asp Ala Leu Ala Thr Ser Thr Leu Pro Phe Gln Ser Val Asn Tyr
            115                 120                 125

Leu Met Gly Thr Trp Pro Phe Gly Thr Ile Leu Cys Lys Ile Val Ile
    130                 135                 140

Ser Ile Asp Tyr Tyr Met Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
        195                 200                 205

Lys Tyr Arg Gln Gly Ser Ile Asp Cys Thr Leu Thr Phe Ser His Pro
    210                 215                 220

Thr Trp Tyr Trp Glu Asn Leu Leu Lys Ile Cys Val Phe Ile Phe Ala
225                 230                 235                 240

Phe Ile Met Pro Ile Leu Ile Ile Thr Val Cys Tyr Gly Leu Met Ile
                245                 250                 255

Leu Arg Leu Lys Ser Val Arg Met Leu Ser Gly Ser Lys Lys Lys Asp
            260                 265                 270

Arg Asn Leu Arg Arg Ile Thr Arg Met Val Leu Val Val Val Ala Val
        275                 280                 285

Thr Ile Val Cys Trp Thr Pro Ile His Ile Tyr Val Ile Ile Lys Ala
    290                 295                 300

Leu Ile Thr Ile Pro Glu Thr Thr Phe Gln Thr Val Ser Trp His Phe
305                 310                 315                 320

Cys Ile Ala Leu Gly Tyr Thr Met Ser Cys Leu Met Pro Val Leu Tyr
                325                 330                 335

Ala Phe Leu Asp Lys Met Thr Lys Arg Cys Thr Arg Glu Phe Cys Ile
            340                 345                 350

Pro Thr Ser Ser Thr Ile Glu Gln Gln Asn Ser Thr Arg Val Arg Gln
        355                 360                 365

Asn Thr Arg Glu His Pro Ser Thr Ala Asn Thr Val Asp Arg Thr Asn
    370                 375                 380

His Gln Leu Glu Asn Leu Glu Ala Glu Thr Ala Pro Leu Pro
385                 390                 395
```

( 2 ) INFORMATION FOR SEQ ID NO:9:

( i ) SEQUENCE CHARACTERISTICS:
        ( A ) LENGTH: 372 amino acids
        ( B ) TYPE: amino acid
        ( C ) TOPOLOGY: linear ( i i ) MOLECULE TYPE:
        ( A ) DESCRIPTION: peptide ( x i ) SEQUENCE DESCRIPTION: SEQ ID NO:9:

```
Met Glu Leu Val Pro Ser Ala Arg Ala Glu Leu Gln Ser Ser Pro Leu
 1               5                  10                  15

Val Asn Leu Ser Asp Ala Phe Pro Ser Ala Phe Pro Ser Ala Gly Ala
                20                  25                  30

Asn Ala Ser Gly Ser Pro Gly Ala Arg Ser Ala Ser Ser Leu Ala Leu
                35                  40                  45

Ala Ile Ala Ile Thr Ala Leu Tyr Ser Ala Val Cys Ala Val Gly Leu
            50                  55                  60

Leu Gly Met Val Leu Val Met Phe Gly Ile Val Arg Tyr Thr Lys Leu
 65                  70                  75                  80

Lys Thr Ala Thr Asn Ile Tyr Ile Phe Met Leu Ala Leu Ala Asp Ala
                85                  90                  95

Leu Ala Thr Ser Thr Leu Pro Phe Gln Ser Ala Lys Tyr Leu Met Glu
               100                 105                 110

Thr Trp Pro Phe Gly Glu Leu Leu Cys Lys Ala Val Leu Ser Ile Asp
           115                 120                 125

Tyr Tyr Lys Met Thr Thr Ser Ile Phe Thr Leu Thr Met Met Ser Val
       130                 135                 140

Asp Arg Tyr Ile Ala Val Cys His Pro Val Lys Ala Leu Asp Phe Arg
145                 150                 155                 160

Thr Pro Ala Lys Ala Lys Leu Ile Met Ile Cys Ile Trp Val Leu Ala
                165                 170                 175

Ser Gly Val Gly Val Pro Ile Met Val Met Ala Val Thr Gln Pro Arg
               180                 185                 190

Asp Phe Ala Val Val Cys Met Leu Gln Phe Pro Ser Pro Ser Trp Tyr
           195                 200                 205

Trp Asp Thr Val Thr Lys Ile Cys Val Phe Leu Phe Ala Phe Val Val
210                 215                 220

Pro Ile Leu Ile Ile Thr Val Cys Tyr Gly Leu Met Leu Leu Arg Leu
225                 230                 235                 240

Arg Ser Val Arg Leu Leu Ser Gly Ser Lys Lys Lys Asp Arg Ser Leu
                245                 250                 255

Arg Arg Ile Thr Arg Met Val Leu Val Val Val Gly Ala Phe Val Val
           260                 265                 270

Cys Trp Ala Pro Ile His Ile Phe Val Ile Val Trp Thr Leu Val Asp
       275                 280                 285

Ile Asn Arg Arg Asp Pro Leu Val Val Ala Ala Leu His Leu Cys Ile
   290                 295                 300

Ala Leu Gly Tyr Ala Met Ser Ser Leu Met Pro Val Leu Tyr Ala Phe
305                 310                 315                 320

Leu Asp Lys Lys Thr Lys Arg Cys Thr Arg Gln Leu Cys Arg Thr Pro
                325                 330                 335

Cys Gly Arg Gln Glu Pro Gly Ser Leu Arg Arg Pro Arg Gln Ala Thr
           340                 345                 350
```

```
Thr  Arg  Glu  Arg  Val  Thr  Ala  Cys  Thr  Pro  Ser  Asp  Gly  Pro  Gly  Gly
          355                     360                     365

Gly  Ala  Ala  Ala
          370
```

(2) INFORMATION FOR SEQ ID NO:10:

(i) SEQUENCE CHARACTERISTICS:
        (A) LENGTH: 378 amino acids
        (B) TYPE: amino acid
        (C) TOPOLOGY: linear (ii) MOLECULE TYPE:
        (A) DESCRIPTION: peptide (xi) SEQUENCE DESCRIPTION: SEQ ID NO:10:

```
Met  Glu  Ser  Pro  Ile  Gln  Ile  Phe  Arg  Gly  Asp  Pro  Gly  Pro  Thr  Cys
 1                    5                    10                    15

Ser  Pro  Ser  Ala  Cys  Leu  Leu  Pro  Asn  Ser  Ser  Ser  Trp  Phe  Pro  Asn
               20                    25                    30

Trp  Ala  Glu  Ser  Asp  Ser  Asn  Gly  Ser  Val  Gly  Ser  Glu  Asp  Gln  Gln
          35                    40                    45

Leu  Glu  Ser  Ala  His  Ile  Ser  Pro  Ala  Ile  Pro  Val  Ile  Ile  Thr  Ala
     50                    55                    60

Val  Tyr  Ser  Val  Val  Phe  Val  Val  Gly  Leu  Val  Gly  Met  Ser  Leu  Val
65                        70                    75                         80

Met  Phe  Val  Ile  Ile  Arg  Tyr  Thr  Lys  Met  Lys  Thr  Ala  Thr  Asn  Ile
                    85                    90                         95

Tyr  Ile  Phe  Met  Leu  Ala  Leu  Ala  Asp  Ala  Leu  Val  Thr  Thr  Thr  Met
                    100                   105                   110

Pro  Phe  Gln  Ser  Ala  Val  Tyr  Leu  Met  Asn  Ser  Trp  Pro  Phe  Gly  Asp
          115                   120                   125

Val  Leu  Cys  Lys  Ile  Val  Ile  Ser  Ile  Asp  Tyr  Lys  Lys  Phe  Thr  Ser
     130                   135                   140

Ile  Phe  Thr  Leu  Thr  Met  Met  Ser  Val  Asp  Arg  Tyr  Ile  Ala  Val  Cys
145                       150                   155                        160

His  Pro  Val  Lys  Ala  Leu  Asp  Phe  Arg  Thr  Pro  Leu  Lys  Ala  Lys  Ile
               165                   170                   175

Ile  Trp  Ile  Cys  Ile  Trp  Leu  Leu  Ala  Ser  Ser  Val  Gly  Ile  Ser  Ala
               180                   185                   190

Ile  Val  Leu  Gly  Gly  Thr  Lys  Val  Arg  Glu  Asp  Val  Asp  Val  Ile  Glu
          195                   200                   205

Cys  Ser  Leu  Phe  Pro  Asp  Asp  Glu  Tyr  Ser  Trp  Trp  Asp  Leu  Phe  Met
     210                   215                   220

Lys  Ile  Cys  Val  Phe  Val  Phe  Ala  Phe  Val  Ile  Pro  Val  Leu  Ile  Ile
225                       230                   235                        240

Ile  Val  Cys  Tyr  Thr  Leu  Met  Ile  Leu  Arg  Leu  Lys  Ser  Val  Arg  Leu
                    245                   250                   255

Leu  Ser  Gly  Ser  Arg  Lys  Lys  Asp  Arg  Asn  Leu  Arg  Arg  Ile  Thr  Lys
               260                   265                   270

Leu  Val  Leu  Val  Val  Val  Ala  Val  Phe  Ile  Ile  Cys  Asn  Thr  Pro  Ile
          275                   280                   285

His  Ile  Phe  Ile  Leu  Val  Glu  Ala  Leu  Gly  Ser  Thr  Ser  His  Ser  Thr
     290                   295                   300

Ala  Ala  Leu  Ser  Ser  Tyr  Tyr  Phe  Cys  Ile  Ala  Leu  Gly  Tyr  Thr  Met
305                       310                   315                        320

Ser  Ser  Leu  Met  Pro  Val  Leu  Tyr  Ala  Phe  Leu  Asp  Lys  Asn  Phe  Lys
```

```
                              325                           330                            335
Arg  Cys  Thr  Arg  Asp  Phe  Cys  Phe  Pro  Ile  Lys  Met  Arg  Met  Glu  Arg
                340                     345                      350

Gln  Ser  Thr  Asn  Arg  Val  Arg  Asn  Thr  Val  Gln  Asp  Pro  Ala  Ser  Met
                355                     360                      365

Arg  Asp  Val  Gly  Gly  Met  Asn  Lys  Pro  Val
                370                     375
```

(2) INFORMATION FOR SEQ ID NO:11:

(i) SEQUENCE CHARACTERISTICS:
        (A) LENGTH: 17 amino acids
        (B) TYPE: amino acid
        (C) TOPOLOGY: linear (ii) MOLECULE TYPE:
        (A) DESCRIPTION: peptide (xi) SEQUENCE DESCRIPTION: SEQ ID NO:11:

```
Phe  Gly  Gly  Phe  Thr  Gly  Ala  Arg  Lys  Ser  Ala  Arg  Lys  Leu  Ala  Asn
 1                     5                      10                          15
Gly
```

(2) INFORMATION FOR SEQ ID NO:12:

(i) SEQUENCE CHARACTERISTICS:
        (A) LENGTH: 17 amino acids
        (B) TYPE: amino acid
        (C) TOPOLOGY: linear (ii) MOLECULE TYPE:
        (A) DESCRIPTION: peptide (xi) SEQUENCE DESCRIPTION: SEQ ID NO:12:

```
Tyr  Gly  Gly  Phe  Leu  Arg  Arg  Ile  Arg  Pro  Lys  Leu  Lys  Trp  Asp  Asn
 1                     5                      10                          15
Gly
```

(2) INFORMATION FOR SEQ ID NO:13:

(i) SEQUENCE CHARACTERISTICS:
        (A) LENGTH: 16 amino acids
        (B) TYPE: amino acid
        (C) TOPOLOGY: linear (ii) MOLECULE TYPE:
        (A) DESCRIPTION: peptide (xi) SEQUENCE DESCRIPTION: SEQ ID NO:13:

```
Tyr  Gly  Gly  Phe  Met  Thr  Ser  Glu  Lys  Ser  Gln  Thr  Pro  Leu  Val  Thr
 1                     5                      10                          15
```

(2) INFORMATION FOR SEQ ID NO:14:

(i) SEQUENCE CHARACTERISTICS:
        (A) LENGTH: 13 amino acids
        (B) TYPE: amino acid
        (C) TOPOLOGY: linear (ii) MOLECULE TYPE:
        (A) DESCRIPTION: peptide (xi) SEQUENCE DESCRIPTION: SEQ ID NO:14:

```
Tyr  Gly  Gly  Phe  Leu  Arg  Arg  Gln  Phe  Lys  Val  Val  Thr
 1                     5                      10
```

( 2 ) INFORMATION FOR SEQ ID NO:15:

( i ) SEQUENCE CHARACTERISTICS:
        ( A ) LENGTH: 5 amino acids
        ( B ) TYPE: amino acid
        ( C ) TOPOLOGY: linear ( i i ) MOLECULE TYPE:
        ( A ) DESCRIPTION: peptide ( x i ) SEQUENCE DESCRIPTION: SEQ ID NO:15:

Tyr Gly Gly Phe Leu
1                    5

( 2 ) INFORMATION FOR SEQ ID NO:16:

( i ) SEQUENCE CHARACTERISTICS:
        ( A ) LENGTH: 4 amino acids
        ( B ) TYPE: amino acid
        ( C ) TOPOLOGY: linear ( i i ) MOLECULE TYPE:
        ( A ) DESCRIPTION: peptide ( x i ) SEQUENCE DESCRIPTION: SEQ ID NO:16:

Phe Gly Gly Phe
1

1

MAMMALIAN OPIOID RECEPTOR LIGAND AND USES

This invention was made with government support under National Institute of Health grants R01 MH48991. The government has certain rights to this invention.

BACKGROUND OF THE INVENTION

1. Field of the Invention

This invention relates to opioid receptors from mammalian species and ligands specific for such receptors. Specifically, the invention relates to the isolation of an endogenous peptide ligand specific for a novel mammalian opioid receptor. The invention also relates to the construction of analogues, derivatives and peptide mimetics of this endogenous mammalian opioid receptor ligand. Specifically provided is a mammalian hypothalamus-derived endogenous opioid receptor ligand, synthetic embodiments and analogues thereof. Methods of making and using such ligands, as well as antibodies against and epitopes of this novel opioid receptor ligand are also provided by the invention.

2. Background of the Invention

The use (and abuse) of opiates, archetypally opium and morphine, have been known since antiquity (reviewed in Brownstein, 1993, Proc. Natl. Acad. Sci. USA 90: 5391–5393). Since the nineteenth century, chemical characterization and synthesis of a number of morphine analogues have been achieved in an effort to discover a compound with the analgesic effects of morphine that lacks or is substantially attenuated in its addictive potential. These efforts have proven fruitless to date.

The biology behind the reasons why morphine and morphine-like compounds display both analgesic and addictive properties was first elucidated by the discovery of endogenous morphine-like compounds termed enkephalins (see DiChara & North, 1992, Trends in Pharmacol. Sci. 13: 185–193 for review). Accompanying this finding of an endogenous opiate was the biochemical evidence for a family of related but distinct opiate receptors, each of which displays a unique pharmacological profile of response to opiate agonists and antagonists (see McKnight & Rees, 1991, Neurotransmissions 7: 1–6 for review). To date, four distinct opiate receptors have been described by their pharmacological profiles and anatomical distribution: these comprise the $\mu$, $\delta$, $\kappa$ and $\sigma$ receptors (the $\sigma$ receptor has been determined to be a non-opioid receptor with cross-reactivity to some opioid agonists).

Thus, mammalian opioid receptors are known in the art, and some of these proteins have been isolated biochemically and their corresponding genes have been recently cloned using genetic engineering means.

Kieffer et al., 1992, Proc. Natl. Acad. Sci. USA 89: 12048–12052 disclosed the isolation of a cDNA copy of the mouse b-opioid receptor by expression cloning.

Evans et al., 1992, Science 258: 1952–1955 disclose the isolation of a cDNA copy of the mouse $\delta$-opioid receptor by expression cloning.

Chen et al., 1993, Molec. Pharmacol. 44: 8–12 disclose the isolation of a cDNA copy of the rat $\mu$-opioid receptor.

Yasuda et al., 1993, Proc. Natl. Acad. Sci. USA 90: 6736–6740 disclose the isolation of a cDNA copy of each of the mouse $\kappa$- and $\delta$-opioid receptor.

Bzdega et al., 1993, Proc. Natl. Acad. Sci. USA 90: 9305–9309 disclose the isolation and chromosomal location of the b-opioid receptor in the mouse.

The present inventors have cloned, expressed and functionally characterized a novel mammalian opioid receptor gene, disclosed in co-owned and co-pending U.S. Pat. application, Ser. No. 08/149,093, filed Nov. 8, 1993, now U.S. Pat. No. 5,658,783 which is hereby incorporated by reference in its entirety. Specifically disclosed therein are nucleic acids encoding the novel mammalian opioid receptor gene, recombinant expression constructs comprising this opioid receptor gene, cells containing such constructs and expressing the novel opioid receptor gene, and methods for making and using such nucleic acids, constructs and cells for opioid detection and novel drug screening. The nucleic acid sequence of the MSOR gene and the deduced amino acid sequence of the cognate receptor protein were also disclosed in this prior application.

In 1991, U.S. pharmaceutical companies spent an estimated $7.9 billion on research and development devoted to identifying new therapeutic agents (Pharmaceutical Manufacturer's Association). The magnitude of this amount is due, in part, to the fact that the hundreds, if not thousands, of chemical compounds must be tested in order to identify a single effective therapeutic agent that does not engender unacceptable levels of undesirable or deleterious side effects. There is an increasing need for economical methods of testing large numbers of chemical compounds to quickly identify those compounds that are likely to be effective in treating disease.

This is of particular importance for psychoactive and psychotropic drugs, due to their pharmacological importance and their potential to greatly benefit or greatly harm human patients treated with such drugs. At present, few such economical systems exist. Conventional screening methods require the use of animal brain slices in binding assays as a first step. This is suboptimal for a number of reasons, including interference in the binding assay by non-specific binding of heterologous (i.e., non-receptor) cell surface proteins expressed by brain cells in such slices; differential binding by cells other than neuronal cells present in the brain slice, such as glial cells or blood cells; and the possibility that putative drug binding behavior in animal brain cells will differ from the binding behavior in human brain cells in subtle but critical ways. For these and other reasons, development of in vitro screening methods for psychotropic drugs has numerous advantages and is a major research goal in the pharmaceutical industry. The ability to synthesize human opioid receptor molecules in vitro would represent one way to provide an efficient and economical means for rational drug design and rapid screening of potentially useful compounds.

A great advantage in efforts for developing novel psychotropic drugs which exert their activity (analgesic and otherwise) via binding to mammalian opioid receptors would be to identify the endogenous ligand(s) which bind to such receptors. Certain such ligands have been isolated in the prior art, including the peptides comprising the endorphins and enkephalins (see Jaffe and Martin, 1990, "Opioid Analgesics and Antagonists", in Goodman and Gilman, eds., *The Pharmacological Basis of Therapeutics*, 8th ed. (Pergammon Press, Inc.: New York), Chapter 21, p.485–521). The identification and characterization of additional endogenous ligands would advantageously provide another basis for rational drug design and an appreciation for structural features of such ligands both shared with other opioid receptor ligands and unique for ligands specific for individual receptors or subclasses of receptors.

SUMMARY OF THE INVENTION

This invention provides small, readily-produced peptides that are ligands for a novel mammalian opioid receptor protein having the amino acid sequence identified as SEQ ID Nos.: 5 and 6. Peptides of the invention are characterized as having an amino acid sequence that is the amino acid sequence identified as SEQ ID Nos.: 5 and 6 or a subsequence thereof, amino acid sequence variants of the sequence or subsequence, as well as analogues and derivatives thereof, that are ligands for the novel mammalian opioid receptor protein having the amino acid sequence identified as SEQ ID Nos.: 5 and 6, as well as analogues and derivative thereof.

The peptides of the invention include linear and cyclized peptides, and synthetic analogues and variants thereof. Certain embodiments of such variants include substitution variants, wherein an amino acid residue at one or more positions in the peptide is replaced with a different amino acid residue (including atypical amino acid residues) from that found in the corresponding position of amino acid sequence of the parent peptide of the invention. In a preferred embodiment, the substituted amino acid is tyrosine. Certain other embodiments of peptide variants of the invention include addition variants, wherein such variant peptides may include up to about a total of 10 additional amino acids, covalently linked to either the amino-terminal or carboxyl-terminal extent, or both, of the parent, opioid receptor binding peptide of provided by the invention. Such additional amino acids may also include atypical amino acids. Linear and cyclized embodiments of the amino acid substitution and addition variant peptides are also provided as peptides of the invention. In addition, peptides of the invention may be provided as fusion proteins with other functional targeting agents, such as immunoglobulin fragments. Derivatives of the peptides of the invention also include modifications of the amino-and carboxyl-termini and amino acid side chain chemical groups such as amines, carboxylic acids, alkyl and phenyl groups.

In a first aspect, the invention provides peptides of the formula:

(Xaa)$_n$-Phe-Gly-Gly-Phe-($A^1$)-($A^2$)-($A^3$)-($A^4$)-($A^5$)-($A^6$)-($A^7$)-($A^8$)-($A^9$)-($A^{10}$)-($A^{11}$)-($A^{12}$)-Gln(Xaa)$_m$ wherein $A^1$ is Thr, Leu or Met; $A^2$ is Gly, Arg or Thr; $A^3$ is Ala, Arg or Ser; $A^4$ is Arg, Ile, Glu or Gln; $A^5$ is Lys, Arg or Phe; $A^6$ is Ser, Pro or Lys; $A^7$ is Ala, Lys, Gln or Val; $A^8$ is Arg, Leu, Thr or Val; $A^9$ is Lys, Pro or Thr; $A^{10}$ is Tyr, Leu or Trp; $A^{11}$ is Ala, Asp or Val; $A^{12}$ is Asn, or Thr; (Xaa) is any amino acid; n and m are integers wherein n+m is no more than 82; and the amino acids are each individually in either the D or L stereochemical configuration and the peptide specifically binds to a mammalian opioid receptor having an amino acid sequence identified by Seq ID Nos. :4. In a preferred embodiment, the peptide has the formula:

Phe-Gly-Gly-Phe-Thr-Gly-Ala-Arg-Lys-Ser-Ala-Arg-Lys-Leu-Ala-Asn-Gln (SEQ ID No.:5), and n+m equals zero. In an another preferred embodiment, the peptide has the formula:

Phe-Gly-Gly-Phe-Thr-Gly-Ala-Arg-Lys-Ser-Ala-Arg-Lys-Tyr-Ala-Asn-Gln (SEQ ID No.:6), and n+m equals zero. Both naturally-occurring embodiments of such peptides, purified using well-established techniques from the cells or tissues producing the peptide, and synthetic embodiments, are within the scope of the invention.

In other embodiments of this aspect of the invention are provided peptides of general formula:

(Xaa)$_n$-Phe-Gly-Gly-Phe-($A^1$)-($A^2$)-($A^3$)-($A^4$)-($A^5$)-(A6)-($A^7$)-($A^8$)-($A^9$)-($A^{10}$)-($A^{11}$)-($A^{12}$)-Gln(Xaa)$_m$ and having amino acid substituents as described above wherein such peptides are radiolabeled by conjugation with or binding to a radioactive isotope. In a preferred embodiment, the peptide has the formula:

Phe-Gly-Gly-Phe-Thr-Gly-Ala-Arg-Lys-Ser-Ala-Arg-Lys-Tyr-Ala-Asn-Gln (SEQ ID No.:6), n+m equals zero, and the radiolabel is a radioisotope of iodine. In other preferred embodiments, the peptide is covalently linked to a radiolabel binding moiety and the radiolabel a radioisotope of indium, gallium, technetium, rhenium or other useful radioisotope.

The invention also provides pharmaceutical compositions of the peptides of the invention. In a first aspect, the peptides of the invention are provided in a pharmaceutical composition comprising an acceptable carrier or diluent. In a second aspect, such pharmaceutical compositions are provided in detectably-labeled embodiments, useful for diagnostic identification of sites of both normal and pathological peptide ligand receptor binding in vivo and in vitro. In such embodiments, the peptides of the invention are detectably labeled, for example, with a radioisotope such as I-123, I-125 or I-131, conjugated to the peptide via, inter alia, a tyrosine residue that is non-essential for receptor binding. Additional radioisotopes, such as In-111, Ga-67,Re-186, Re-188 and Tc-99m, can be conjugated to such peptides using methods well-understood in the art. In such embodiments, the pharmaceutical composition is radiolabeled to an appropriate specific activity, and administered to an animal, preferably a human, at a diagnostically-effective and non-toxic dose. Methods and routes of administration may be selected by those with skill in the art based on well-established techniques and in a clinically-appropriate fashion.

In a second aspect of the pharmaceutical compositions of the invention, the opioid receptor-binding ligand peptides are provided in an appropriate composition with acceptable carriers of diluents and in a therapeutically-effective amount. In such embodiments, the therapeutic pharmaceutical compositions are used in methods to treat diseases or pathological conditions associated with ligand binding to the MSOR receptor. Specifically provided are methods for treating locomotor diseases in an animal.

The invention also provides methods for designing MSOR opioid receptor ligands and analogues, derivatives and mimetics thereof, using the amino acid sequence of the peptide ligands of the invention. Also encompassed within the scope of this invention are such analogues, derivatives and mimetics produced by the methods of the invention.

In a second aspect, the invention provides nucleic acids encoding a novel mammalian opioid-specific receptor protein having an amino acid sequence identified as SEQ ID No.:4, recombinant eukaryotic expression constructs capable of expressing the novel mammalian opioid-specific receptor of the invention in cultures of transformed cells, as well as cultures of transformed eukaryotic cells that synthesize the receptor of the invention. The invention also provides homogeneous compositions of the receptor protein having an amino acid sequence identified as SEQ ID No. :4, and antibodies against and epitopes of the receptor protein of the invention. Methods for characterizing these receptor proteins and methods for using these proteins in the development of agents having pharmacological uses related to these receptors are also provided by the invention.

In this aspect of the invention is provided a nucleic acid having a nucleotide sequence encoding a mammalian MSOR opioid receptor. In a preferred embodiment, the nucleic acid encodes 1452 nucleotides of the cDNA comprising 1101 nucleotides of coding sequence, 181 nucleotides of 5' untranslated sequence and 170 nucleotides of 3' untranslated sequence, depicted in FIG. 1 and identified as SEQ ID No:3. Encompassed in this aspect of the invention is the disclosed sequence and allelic variants of this sequence, either naturally occurring or the product of in vitro chemical or genetic modification.

The corresponding receptor protein, having the deduced amino acid sequence shown in FIG. 1 and identified as SEQ ID No.:4, is also an aspect of the invention. In particular embodiments of this aspect of the invention is comprised a homogeneous composition of the 47 kD mammalian opioid receptor protein and derivatives thereof, said size being understood to be the size of the protein before any post-translational modifications. The amino acid sequence of this 47 kD receptor protein is depicted in FIG. 1 and identified as SEQ ID No:4.

This invention provides both nucleotide and amino acid sequence probes derived from the sequences herein provided, isolated from either cDNA or genomic DNA, as well as probes made synthetically with the sequence information derived therefrom. The invention specifically includes but is not limited to oligonucleotide, nick-translated, random primed, or in vitro amplified probes made using cDNA or genomic clones embodying this aspect of the invention, and oligonucleotide and other synthetic probes synthesized chemically using the nucleotide sequence information of cDNA or genomic clone embodiments of the invention.

The present invention also includes synthetic peptides made using the nucleotide sequence information comprising the cDNA embodiments of the receptor protein embodiments of the invention. The invention includes either naturally occurring or synthetic peptides which may be used as antigens for the production of receptor-specific antibodies, or useful as competitors of receptor molecules for agonist, antagonist or drug binding, or to be used for the production of inhibitors of the binding of agonists or antagonists or analogues thereof to such MSOR receptor molecules. Particularly preferred embodiments of this aspect of the invention are such peptides that interact with the peptide ligand embodiments of the invention and enhance or inhibit peptide ligand binding to the receptor protein.

The present invention also provides antibodies against and epitopes of the mammalian opioid receptor molecules of the invention, including antisera and both polyclonal and monoclonal embodiments of such antibodies and hybridoma cell lines producing such monoclonal antibodies.

The present invention provides recombinant expression constructs comprising a nucleic acid encoding a mammalian MSOR receptor of the invention wherein the construct is capable of expressing the encoded MSOR receptor in cultures of cells transformed with the construct. Preferred embodiments of such constructs comprise the MSOR receptor cDNA depicted in FIG. 1 (SEQ ID No.:3), such constructs being capable of expressing the MSOR receptor encoded therein in cells transformed with the construct.

The invention also provides cultures cells transformed with the recombinant expression constructs of the invention, each such cultures being capable of and in fact expressing the mammalian MSOR receptor encoded in the transforming construct.

The present invention also includes within its scope protein preparations of prokaryotic and eukaryotic cell membranes containing the MSOR receptor protein of the invention, derived from cultures of prokaryotic or eukaryotic cells, respectively, transformed with the recombinant expression constructs of the invention.

The invention also provides methods for screening compounds for their ability to inhibit, facilitate or modulate the biochemical activity of the mammalian MSOR receptor molecules of the invention, for use in the in vitro screening of novel agonist and antagonist compounds. In preferred embodiments, cells transformed with a recombinant expression construct of the invention are contacted with such a compound, and the binding capacity of the compounds, as well as the effect of the compound on binding of other, known opioid agonists and antagonists, is assayed. Additional preferred embodiments comprise quantitative analyses of such effects. The invention specifically provides a method for screening a compound for a capacity to bind to a mammalian MSOR opioid receptor in cells expressing the receptor, using a competitive assay between the compound to be tested and the peptide ligands of the invention. The method comprises the steps of:

(a) transforming a culture of eukaryotic or prokaryotic cells with a recombinant expression construct capable of expressing a mammalian MSOR opioid receptor having an amino acid sequence identified as SEQ ID No. :4, wherein the cells of the transformed cell culture express the opioid receptor;

(b) assaying the transformed cell culture for binding of an amount of a detectably-labeled peptide according to claim 1 in competition with varying amounts of the compound; and (c) determining whether the compound competitively binds to the opioid receptor by calculating the extent of inhibition of binding of the detectably-labeled peptide in the presence of the compound.

In additional embodiments of this method is included the additional step of:

(d) comparing the binding capacity of the compound with the binding capacities of additional compounds that are known to bind to mammalian opioid receptors, wherein said additional compounds comprise naturally-occurring and synthetic opioid receptor agonists and antagonists.

The present invention is also useful for the detection of analogues, agonists or antagonists, known or unknown, of the mammalian MSOR receptors of the invention, either naturally occurring or embodied as a drug. In preferred embodiments, such analogues, agonists or antagonists may be detected in blood, saliva, semen, cerebrospinal fluid, plasma, lymph, or any other bodily fluid. In particularly preferred embodiments, the peptide ligands of the invention are used in competitive binding assays to quantitatively evaluate novel ligand binding to the MSOR receptor.

Specific preferred embodiments of the present invention will become evident from the following more detailed description of certain preferred embodiments and the claims.

DESCRIPTION OF THE DRAWINGS

FIG. 1 illustrates the nucleotide (SEQ ID No.:3) and amino acid (SEQ ID No.:4) sequences of the novel mammalian MSOR opioid receptor of the invention.

FIG. 2 presents an amino acid (SEQ ID NOS: 7, 8, 9 and 10)sequence comparison between the novel mammalian MSOR opioid receptor protein of the invention (designated LC132) and the rat $\mu$-opioid receptor, and the mouse $\delta$- and $\kappa$-opioid receptor proteins.

FIG. 7 is a comparison of the amino acid (SEQ ID NOS: 11, 12, 13, 14 and 15) sequence of orphanin FQ and other opioid receptor binding peptides; identical amino acid residues shared between the peptides are shown in boldface.

DETAILED DESCRIPTION OF THE PREFERRED EMBODIMENTS

Figure 1A:
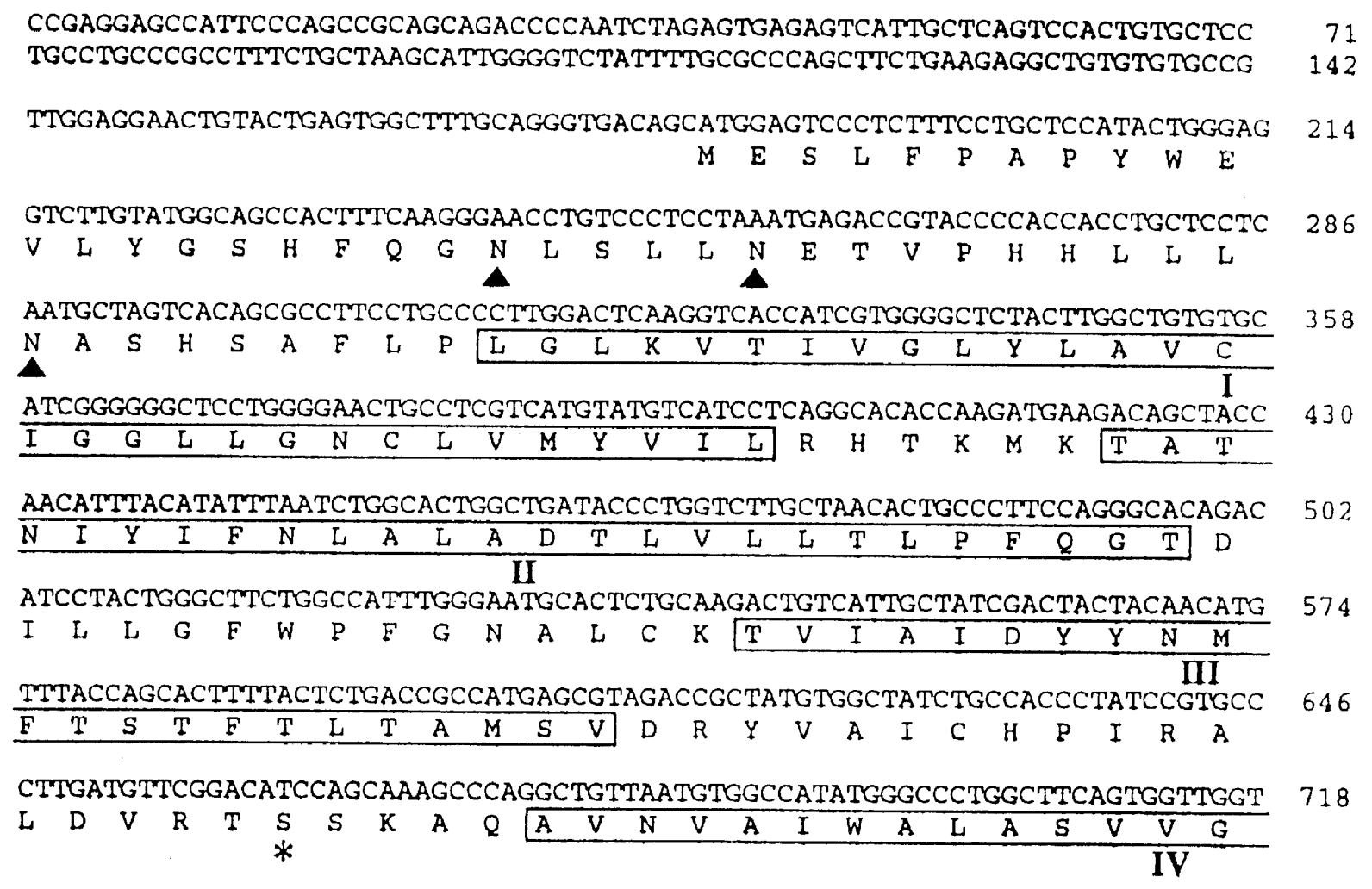
Figure 3:
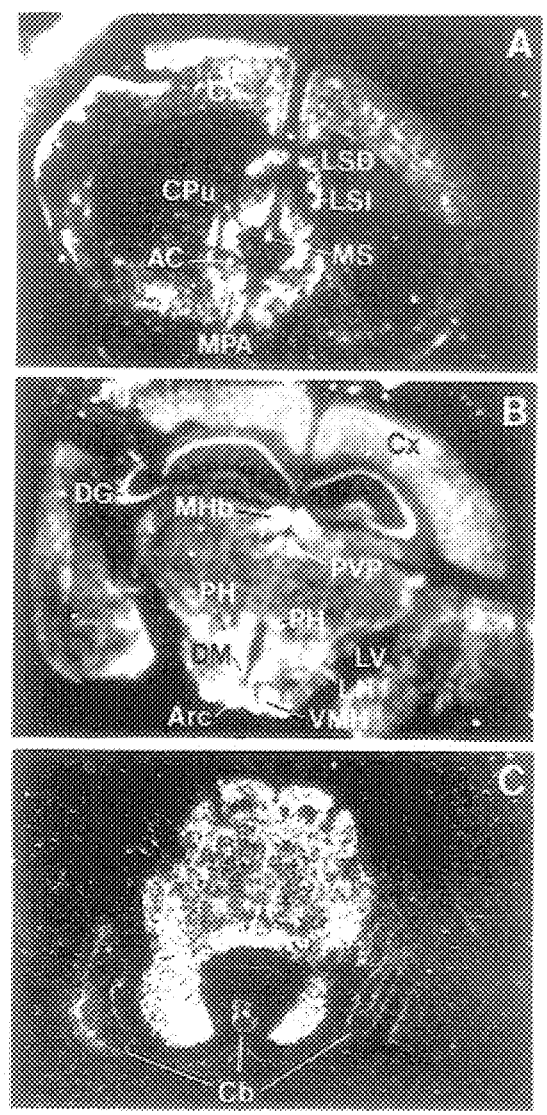
FIG. 3 illustrates in situ hybridization of rat brain sections with a nucleic acid hybridization probe specific for the mammalian receptor of the invention.

The term "novel mammalian opioid receptor" and "MSOR" as used herein refers to proteins consisting essentially of, and having substantially the same biological activity as, the protein encoded by the nucleic acid depicted in FIG. 1 (SEQ ID No.:3). This definition is intended to encompass natural allelic variations in the disclosed MSOR sequence. Cloned nucleic acid provided by the present invention may encode MSOR protein of any species of origin, including, for example, mouse, rat, rabbit, cat, and human, but preferably the nucleic acid provided by the invention encodes MSOR receptors of mammalian, most preferably rat and human, origin.

The nucleic acids of the invention comprise nucleic acid hybridization probes comprising DNA or RNA consisting essentially of the nucleotide sequence of the MSOR receptor, depicted in FIG. 1 (SEQ ID No.:3), or any portion thereof effective in nucleic acid hybridization. Mixtures of such nucleic acid hybridization probes are also within the scope of this embodiment of the invention. Nucleic acid probes as provided herein are useful for detecting MSOR receptor gene expression in cells and tissues using techniques well-known in the art, including but not limited to Northern blot hybridization, in situ hybridization and Southern hybridization to reverse transcriptase—polymerase chain reaction product DNAs. The probes provided by the present invention, including oligonucleotides probes derived therefrom, are useful are also useful for Southern hybridization of mammalian, preferably human, genomic DNA for screening for restriction fragment length polymorphism (RFLP) associated with certain genetic disorders The invention provides an isolated and purified, naturally-occurring, endogenous mammalian peptide ligand that specifically binds to the MSOR receptor of the invention. For the purposes of this invention it will be understood that a ligand is any biologically active molecule that specifically binds to an MSOR opioid receptor of the invention. The ligands of the invention include synthetic embodiments of the naturally-occurring peptide ligand isolated as described herein, as well as analogues, derivatives and variants of this peptide that specifically bind to the MSOR receptor. Such analogues include substitution variants, wherein an amino acid is substituted conservatively with another amino acid that does not ablate the specific binding properties of the peptide ligand. Specifically provided by the invention are substitution variants wherein the substituted amino acid is Leu$^4$, wherein this residue is substituted with tyrosine. Specifically provided by the invention are substitution variants wherein the substituted amino acid is Phe$^1$, wherein this residue is substituted with tyrosine.

Each peptide ligand of the invention is comprised of a sequence of amino acids. The term amino acid as used in this invention is intended to include all L- and D- amino acids, naturally occurring and otherwise.

Generally, those skilled in the art will recognize that peptides as described herein may be modified by a variety of chemical techniques to produce compounds having essentially the same activity as the unmodified peptide, and optionally having other desirable properties. For example, carboxylic acid groups of the peptide, whether carboxyl-terminal or sidechain, may be provided in the form of a salt of a pharmaceutically-acceptable cation or esterified to form a $C_1$–$C_{16}$ ester, or converted to an amide of formula $NR_1R_2$ wherein $R_1$ and $R_2$ are each independently H or $C_1$–$C_{16}$ alkyl, or combined to form a heterocyclic ring, such as 5- or 6-membered. Amino groups of the peptide, whether amino-terminal or sidechain, may be in the form of a pharmaceutically-acceptable acid addition salt, such as the HCl, HBr, acetic, benzoic, toluene sulfonic, maleic, tartaric and other organic salts, or may be modified to $C_1$–$C_{16}$ alkyl or dialkyl amino or further converted to an amide. Hydroxyl groups of the peptide sidechain may be converted to $C_1$–$C_{16}$ alkoxy or to a $C_1$–$C_{16}$ ester using well-recognized techniques. Phenyl and phenolic rings of the peptide sidechain may be substituted with one or more halogen atoms, such as fluorine, chlorine, bromine or iodine, or with $C_1$–$C_{16}$ alkyl, $C_1$–$C_{16}$ alkoxy, carboxylic acids and esters thereof, or amides of such carboxylic acids. Methylene groups of the peptide sidechains can be extended to homologous $C_2$–$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced binding and/or stability. For example, a carboxyl-terminal or amino-terminal cysteine residue can be added to the peptide, so that when oxidized the peptide will contain a disulfide bond, thereby generating a cyclic peptide. Other peptide cyclizing methods include the formation of thioethers and carboxyl- and amino-terminal amides and esters.

Peptidomimetic and organomimetic embodiments are also hereby explicitly declared to be within the scope of the present invention, whereby the three-dimensional arrangement of the chemical constituents of such peptido- and organomimetics mimic the three-dimensional arrangement of the peptide backbone and component amino acid sidechains in the peptide, resulting in such peptido- and organomimetics of the peptides of this invention having substantial biological activity. For computer modelling applications, a pharmacophore is an idealized, three-dimensional definition of the structural requirements for biological activity. Peptido- and organomimetics can be designed to fit each pharmacophore with current computer modelling software (computer aided drug design). The degree of overlap between the specific activities of pharmacophores remains to be determined. It will be understood that mimetics prepared using such techniques that specifically bind to the MSOR receptor and developed using the peptide ligands of the invention will fall within the scope of the appended claims.

The peptides provided by the present invention can be chemically synthesized by any of a number of manual or automated methods of synthesis known in the art. Automated synthetic routines such as those available for use with automated peptide synthesizers are also intended to come within the scope of the present invention. Chemical derivatization, using the methods disclosed in this specification or other methods well known in the art, of naturally-occurring peptides or peptides purified from mixtures of protein degradation products, degraded by enzymatic or chemical means, are also within the scope of this invention, as are peptides made by molecular or genetic engineering means. Preferably, solid phase peptide synthesis (SPPS) is carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzo-triazol-1-yl)- 1,1,3,3-tetramethyluronium hexafluorophosphate/hydroxybenzotriazole (HBTU/HOBT), and using p-hydroxymethylphenoxymethylpolystyrene (HMP) or Sasrin™ resin for carboxyl-terminus acids or Rink amide resin for carboxyl-terminus amides.

Fmoc-derivatized amino acids are prepared from the appropriate precursor amino acids by tritylation with triphenylmethanol in trifluoroacetic acid, followed by Fmoc derivitization as described by Atherton et al. (1989, *Solid Phase Peptide Synthesis*, IRL Press: Oxford).

Sasrin™ resin-bound peptides are cleaved using a solution of 1 % TFA in dichloromethane to yield the protected peptide. Where appropriate, protected peptide precursors are cyclized between the amino- and carboxyl-termini by reaction of the amino-terminal free amine and carboxyl-terminal free acid using diphenylphosphorylazide in nascent peptides wherein the amino acid sidechains are protected.

HMP or Rink amide resin-bound products are routinely cleaved and protected sidechain-containing cyclized peptides deprotected using a solution comprised of trifluoroacetic acid (TFA), optionally also comprising water, thioanisole, and ethanedithiol, in ratios of 100:5 5:2.5, for 0.5–3 hours at room temperature.

Crude peptides are purified by preparative high pressure liquid chromatography (HPLC) using a Waters Delta-Pak C18 column and gradient elution with 0.1% TFA in water modified with acetonitrile. After column elution, acetonitrile is evaporated from the eluted fractions, which were then lyophilized. The identity of each product so produced and purified is confirmed by fast atom bombardment mass spectroscopy (FABMS) or electrospray mass spectroscopy (ESMS).

The production of proteins such as the opioid receptor proteins of the invention from cloned genes by genetic engineering means is well known in this art. The discussion which follows is accordingly intended as an overview of this field, and is not intended to reflect the full state of the art.

DNA encoding an opioid receptor may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the nucleic acid sequence information from the opioid receptor (MSOR) disclosed herein. Probes may be labeled with any detectable group and used in conventional hybridization assays, as described in greater detail in the Examples below. In the alternative, amino acid transporter-derived nucleic acid sequences may be obtained by use of the polymerase chain reaction (PCR) procedure, using PCR oligonucleotide primers corresponding to nucleic acid sequence information derived from an MSOR receptor as provided herein. See U.S. Pat. Nos. 4,683,195 to Mullis et al. and 4,683,202 to Mullis.

Opioid receptor protein may be synthesized in host cells transformed with a recombinant expression construct comprising a nucleic acid encoding the opioid receptor cDNA. For the purposes of this invention, a recombinant expression construct is a replicable DNA construct in which a nucleic acid encoding an opioid receptor is operably linked to suitable control sequences capable of effecting the expression of the opioid receptor in a suitable host. Generally, control sequences include a transcriptional promoter, an optional operator sequence to control transcription, a sequence encoding suitable mRNA ribosomal binding sites, and sequences which control the termination of transcription and translation. See, Sambrook et al., 1990, *Molecular Cloning: A Laboratory Manual* (Cold Spring Harbor Press: New York).

Vectors useful for practicing the present invention include plasmids, viruses (including phage), retroviruses, and integratable DNA fragments (i.e., fragments integratable into the host genome by homologous recombination). A preferred vector is RcRVS (Invitrogen, San Diego, Calif.).

Cultures of cells derived from multicellular organisms are a desirable host for recombinant opioid receptor protein synthesis. Transformed host cells are cells which have been transformed or transfected with recombinant expression constructs made using recombinant DNA techniques and comprising nucleic acid encoding an amino acid transporter protein. Transformed host cells may express the opioid receptor protein; when expressed, the opioid receptor of the invention will typically be located in the host cell membrane. See, Sambrook et al., ibid. In principal, any higher eukaryotic cell culture is useful, whether from vertebrate or invertebrate culture. However, mammalian cells are preferred, as illustrated in the Examples. Propagation of such cells in cell culture has become a routine procedure. See *Tissue Culture*, Academic Press, Kruse & Patterson, editors (1973). Examples of useful host cell lines are human 293 cells, VERO and HeLa cells, Chinese hamster ovary (CHO) cell lines, mouse Ltk⁻ cell lines and WI138, BHK, COS-7, CV, and MDCK cell lines. CHO cells, COS-7 cells and Ltk⁻ cells are preferred.

The recombinant expression constructs of the present invention are useful to transform cells which do not ordinarily express an opioid receptor to thereafter express the receptor. Such cells are useful as intermediates for making cell membrane preparations useful for receptor binding activity assays, which are in turn useful for drug screening. The recombinant expression constructs of the present invention thus provide a method for obtaining reagents for screening potentially useful drugs at advantageously lower cost than conventional animal screening protocols. While not completely eliminating the need for ultimate in vivo activity and toxicology assays, the constructs and cultures of the invention provide an important first screening step for the vast number of potentially useful psychoactive drugs synthesized, discovered or extracted from natural sources each year.

The recombinant expression constructs of the present invention are useful to detect, isolate, characterize and identify novel endogenous opioid receptor agonists and antagonists found in plasma, serum, lymph, cerebrospinal fluid, seminal fluid, or other potential sources of such compounds.

The utility of the present invention for using the nucleic acids of the invention to produce cell membranes containing the opioid receptor protein encoded thereby, and the demonstrated utility of this aspect of the invention to permit the isolation, characterization and identification of a novel peptide, termed orphanin FQ herein, as an endogenous receptor-binding ligand, enables rational drug design of novel therapeutically-active drugs using currently-available techniques (see Walters, "Computer-Assisted Modeling of Drugs", in Klegerman & Groves, eds., 1993, *Pharmaceutical Biotechnology*, Interpharm Press:Buffalo Grove, Ill., pp. 165–174).

The invention provides homogeneous compositions of a novel mammalian opioid receptor protein produced by transformed eukaryotic cells as provided herein. Each such homogeneous composition is intended to be comprised of the MSOR receptor protein that comprises at least 90% of the protein in such a homogenous composition. The invention also provides membrane preparations from cells expressing the MSOR receptor protein as the result of transformation with a recombinant expression construct, as described herein.

Mammalian opioid receptor proteins made from cloned genes in accordance with the present invention may be used for screening opioid analogues, or agonists or antagonists of opioid binding, or for determining the amount of such agonists or antagonists are present in a solution of interest (e.g., blood plasma, cerebrospinal fluid or serum). For example, host cells may be transformed with a recombinant expression construct of the present invention, a mammalian MSOR receptor expressed in those host cells, and the cells or membranes thereof used to screen compounds for their effect on opioid agonist binding activity. By selection of host cells that do not ordinarily express a MSOR receptor, pure preparations of membranes containing the transporter can be obtained.

The invention also provides ligands for such MSOR receptor proteins, including naturally-occurring ligands and synthetic embodiments thereof. Methods for identifying other, alternative ligands, and agonists and antagonists of peptide ligand binding are also provided by the invention. Such methods include competitive binding assays, wherein the peptide ligands of the invention are detectably labeled and incubated under competitive binding conditions with varying amounts of any putative ligand compound to be tested. The extent of inhibition of labeled ligand binding is useful in characterizing the extent and affinity of binding of novel ligands to the MSOR receptor. Specificity of binding can also be determined using such assays. Preferably, the peptide ligand of the invention being used in such competition experiments is detectably labeled with a radioisotope, such as I-123, I-125 and 1-131.

The invention also provides antibodies that are immunologically reactive to the opioid receptor protein or epitopes thereof provided by the invention. The antibodies provided by the invention may be raised using methods well known in the art.

The present invention also provides monoclonal antibodies that are immunologically reactive with an epitope derived from an MSOR receptor of the invention, or fragment thereof. Such antibodies are made using methods and techniques well known to those of skill in the art. Monoclonal antibodies provided by the present invention are produced by hybridoma cell lines, that are also provided by the invention and that are made by methods well known in the art.

The ligands of the invention are useful as diagnostic and therapeutic agents when constituted as pharmaceutical compositions with the appropriate carriers or diluents. In diagnostic embodiments, detectably-labeled peptide ligands are used in methods for diagnosing diseases or pathological conditions related to ligand binding of MSOR receptors in vivo. Similarly, therapeutic methods of treatment are encompassed by the invention and provided using pharmaceutical compositions of such peptides administered in vivo in therapeutically-effective amounts.

Preparation of pharmaceutically acceptable compositions of the peptides of the present invention can be accomplished using methods well known to those with skill in the art. Any of the common carriers such as sterile saline solution, plasma, etc., can be utilized with the peptides provided by the invention. Routes of administration include but are not limited to oral, intravenous, parenteral, rectal, optical, aural and transdermal. Peptides of the invention may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, buffers, preservatives and the like. Among the preferred media are normal saline and plasma.

Embodiments of the invention comprising medicaments can be prepared for oral administration, for injection, or other parenteral methods and preferably include conventional pharmaceutically acceptable carriers, adjuvents and counterions as would be known to those of skill in the art. The medicaments are preferably in the form of a unit dose in solid, semi-solid and liquid dosage forms such as tablets, pills, powders, liquid solutions or suspensions, and injectable and infusible solutions. Effective dosage ranges from about 100 $\mu$g/kg to about 10 mg/kg of body weight are contemplated.

The invention also provides methods for detecting the amount of an analyte in a solution wherein the analyte is an endogenous peptide ligand of the invention in a biological sample, such as blood, serum, plasma or cerebrospinal fluid. In such methods is provided a first mixture comprised of cells or membranes heterologously expressing the MSOR opioid receptor of the invention, a second mixture comprised of a standard amount of a detectably-labeled embodiment of the peptide ligands of the invention, and a third mixture comprised of a diagnostically- significant tissue sample or bodily fluid. From these mixtures is produced a specific binding reaction mixture by contacting the first, second and third mixtures and incubating the reaction mixture for a time sufficient to allow binding between the peptide ligand and the MSOR receptor. The extent of the binding reaction is determined by calculating the amount of the detectably-labeled peptide ligand of the invention bound to the MSOR receptor, and comparing the amount of binding of the peptide ligand to the MSOR receptor in the presence of the tissue sample or bodily fluid of the third provided mixture with the amount of binding found in the absence of the tissue sample or bodily fluid of the third provided mixture.

The Examples which follow are illustrative of specific embodiments of the invention, and various uses thereof. They set forth for explanatory purposes only, and are not to be taken as limiting the invention.

EXAMPLE 1

Isolation of a Mammalian Opioid Receptor Probe by Random PCR Amplification of Rat Brain-derived cDNA Using Degenerate Oligonucleotide Primers In order to clone novel mammalian G-protein coupled receptors, cDNA prepared from RNA from different regions of mammalian (rat) brain was used as template for a polymerase chain reaction (PCR)-based random cloning experiment. PCR was performed using a pair of degenerate oligonucleotide primers derived from a mouse δ-opioid receptor (Kieffer et al., 1992, Proc. Natl. Acad. Sci. USA 89: 12048–12052; Evans et al., 1992, Science 258: 1952–1955). PCR products obtained in this experiment were characterized by nucleotide sequencing and used to isolate a full-length cDNA from a rat brain cDNA library.

The PCR amplification experiments were performed as described in co-owned and co-pending U.S. Ser. No. 08/149, 093, incorporated by reference, using the following primers:

Primer III (sense):

ATGAATTCAC(G/A/C/T)(A/G)T(G/C)ATGAG(C/T)GT(G/C)GAC(C/A)G(C/A)TA
(SEQ ID NO:1)
and
Primer VII (antisense):

TTGTCGAC(G/A)TA(G/A)AG(A/G)A(T/C)(G/A/C/T)GG(G/A)TT
(SEQ ID NO:2).

Amplified products of the PCR reaction were separated on a 1.0% agarose gel (see Sambrook et al., ibid.), and fragments ranging in size from 400 basepairs (bps) to 750 bp were subcloned in the plasmid vector pBluescript (Stratagene, Lajolla, Calif.). A multiplicity of bacterial colonies comprising each of the subcloned fragments were used to make bacterial colony lifts on nitrocellulose filters using conventional techniques (see Sambrook, et al., ibid.). Such filters were hybridized with a [$^{32}$P]-dCTP-labeled radioactive nucleic acid probe comprising a full-length mouse δ-opioid receptor cDNA at a concentration of 1×10$^6$ cpm/ mL under low stringency hybridization conditions [35% formamide, 5X standard citrate saline (SSC; wherein 1X SSC is 0.15 M NaCl/0.015 M sodium citrate, pH 7.0), 5X Denhardt's solution (wherein 1X Denhardt's solution is 0.02 g/mL each of bovine serum albumin, Ficoll and polyvinylpyrrolidone)] at 37° C. overnight. After hybridization, the filters were washed in a solution of 2X SSC/0.1% sodium dodecyl sulfate (SDS) at 55° C. and then exposed to X-ray film (XAR-5, Eastman-Kodak, Rochester, N.Y.) for 2 days at −70° C. using tungsten-impregnated intensifying screens (DuPont-NEN, Wilmington, Del.). Plasmid DNA from hybridizing clones was purified and the nucleotide sequence of the insert cDNA determined by the dideoxynucleotide chain termination method (Sanger et al., 1977, Proc. Natl. Acad. Sci. USA 74: 5463–5467) using Sequenase® (U.S. Biochemical Corp., Cleveland, Ohio).

EXAMPLE 2

Isolation of a Novel Mammalian Opioid Receptor cDNA

One of the PCR products (termed LC132) were isolated and sequenced in this way and were fund to have a high degree of homology to the mouse δ-opioid receptor sequence (Evans et al., ibid. and Kieffer et al., ibid.). A full-length cDNA clone corresponding to this PCR fragment was isolated from a cDNA library prepared in the cloning vector λgt11 comprising oligo(dT)-primed rat brain cDNA, as described in co-owned and c-pending U.S. Ser. No. 07/149,093.

Nucleotide sequence analysis performed essentially as described (see, Sambrook, ibid.) revealed the sequence shown in FIG. 1 (SEQ ID No.: 3). The putative protein product of the gene is also shown in FIG. 1 (SEQ ID No:4). The sequence was found to have an open reading frame comprising 1101 nucleotides encoding a protein 367 amino acids in length, and having a predicted molecular weight of 47 kilodaltons prior to post-translational modification. The sequence immediately 5' to the proposed initiation codon was found to contain several translation termination codons in-frame with the open reading frame, supporting the assignment of the translation start site. Predicted transmembrane domains [using the algorithm of Eisenberg et al. (1984, J. Molec. Biol. 179: 125–142)] are boxed and identified by Roman numerals (I–VII), and three sites of possible N-linked glycosylation are identified in the amino-terminal portion of the protein with solid triangles. Potential protein phosphorylation sites found in predicted cytoplasmic loops are marked with an asterisk. Further, a pair of cysteine residues conserved among known opioid receptors were found in the first and second predicted extracellular loops. On the basis of this analysis, this cloned nucleic acid was determined to be a novel mammalian opioid receptor. Comparison of the amino acid sequence of the novel receptor with the amino acid sequences of other known mammalian opioid receptors supported this conclusion.

The predicted amino acid sequences of this novel opioid receptor, the rat μ-opioid receptor (Chen et al., ibid.), the mouse δ-opioid receptor (Evans et al., ibid. and Kieffer et al., ibid.) and the mouse κ-Opioid receptor (Yasuda et al., ibid.) are aligned in FIG. 2. Overbars indicate predicted transmembrane regions I through VII in the protein product of the genes. Amino acid residues that are found in common between all four mammalian opioid receptors are presented in boldface.

Overall, the novel mammalian receptor disclosed herein had 47% overall identity with the other mammalian opioid receptors, which similarity rose to 67% when only the predicted transmembrane domains were considered. A more detailed comparison of these amino acid sequences are quantified in Table I, showing the percentage extent of homology in pairwise fashion between the different opioid receptors. Comparisons are made individually at each transmembrane domain (TMI–TMVII), as an average over all transmembrane domains (TMavg) and as the average degree of amino acid sequence homology for each protein as a whole (avg/all). In total, 145 of the 367 residues are shared with the other mammalian opioid receptors, confirming the conclusion that the novel mammalian receptor disclosed herein is an opioid receptor.

EXAMPLE 3

Construction of a Recombinant Expression Construct, DNA Transfection and Functional Expression of the Novel Mammalian Opioid Receptor In order to biochemically characterize the novel mammalian opioid receptor described in Example 2, and to confirm that it encodes a novel opioid receptor, the cDNA was cloned into a mammalian expression construct, the resulting recombinant expression construct transfected into COS-7 cells (for transient expression assays) and mouse Ltk⁻ cells (for stable expression assays), and cell membranes (COS-7) or cell lines (Ltk⁻) were generated that expressed the receptor protein in cellular membranes at the cell surface. Such cells and membranes isolated from such cells were used for biochemical characterization experiments as described in U.S. Ser. No. 149,093.

The entire coding region of the receptor cDNA insert was subcloned in to the RcRSV vector (Invitrogen, San Diego, Calif.) using conventional techniques (see Sambrook et al., ibid.). Such recombinant expression constructs were introduced into COS-7 cells using the calcium-phosphate precipitation technique (Chen & Okayama, 1987, Molec. Cell. Biol. 7: 2745–2752), the transfected cells allowed to express the receptor for between 24–96 hours, and then cell membranes containing the receptor were isolated. The protein concentration was adjusted to 15–80 $\mu$g/sample for each of the binding studies described below.

These recombinant expression constructs were also introduced into Ltk⁻ cells using the calcium-phosphate precipitation technique, and stably-transfected clones were selected by growth in the mammalian neomycin analog G418 (Grand Island Biological Co., Long Island, N.Y.), as the vector RcRSV contains a functional copy of a bacterial neomycin resistance gene. Stable cell lines were then selected for membrane binding studies based on mRNA expression levels of individual neomycin-resistant transfected clones determined by Northern analysis (see Sambrook et al., ibid.). Cell membranes were prepared and used as described above for COS-7 cell transfectants.

Specific binding assays using a variety of opioid receptor agonists and antagonists were performed on membranes from both transient and stable transfectants. Ligand binding experiments were performed essentially as described in Bunzow et al. (1988, Nature 336: 783 – 787)], and U.S. Ser. No. 08/149,093). In binding experiments, increasing amounts of membrane protein (from 15–80 $\mu$g) was incubated with the radioactively-labeled opioid agonist or antagonist to be tested for 120 min at 22° C. in a total volume of 1 ml. However, in these experiments no specific binding was found for the following compounds (their known receptor binding specificities are noted in parentheses): [$^3$H]-Tyr-DAla-Gly-Met-Phe-Gly-ol (DAMGO; $\mu$-opioid receptor agonist), [$^3$H]-c[D-penicillamine$^2$, D-penicillamine$^5$]enkephalin (DPDPE; $\delta$agonist), [$^3$H]-U-69,593 ($\kappa$agonist), [$^3$H]-diprenorphine ($\mu$agonist), [$^3$H]-bremacozine ( $\kappa$agonist), [$^3$H]-dihydromorphine ($\mu$agonist), [$^3$H]-ethylketocyclazocine ($\kappa$agonist) or [$^{125}$I ]-$\beta$-endorphin. Although low levels of specific binding were seen using [$^3$H]-naloxone ($\mu$antagonist), the significance of these results was compromised by the fact that untransfected COS-7 and Ltk⁻ cells also shown endogenous low levels of specific [$^3$H]-naloxone binding.

Figure 4A:
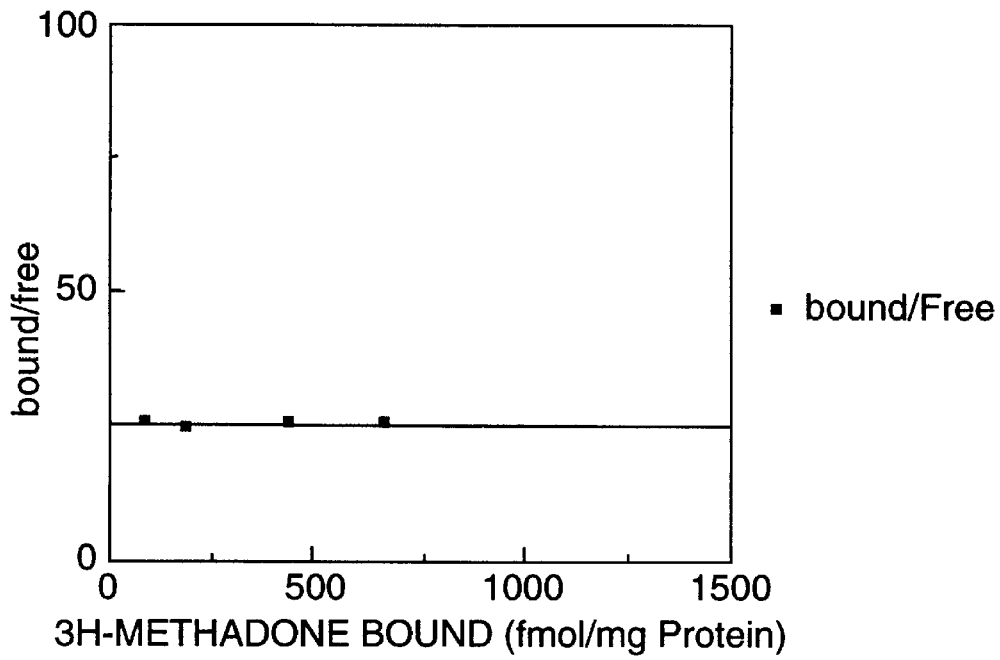
FIG. 4 presents affinity binding experiment results of $^3$H-methadone binding to COS-7 cells expressing the novel mammalian receptor of the invention.
Figure 4B:
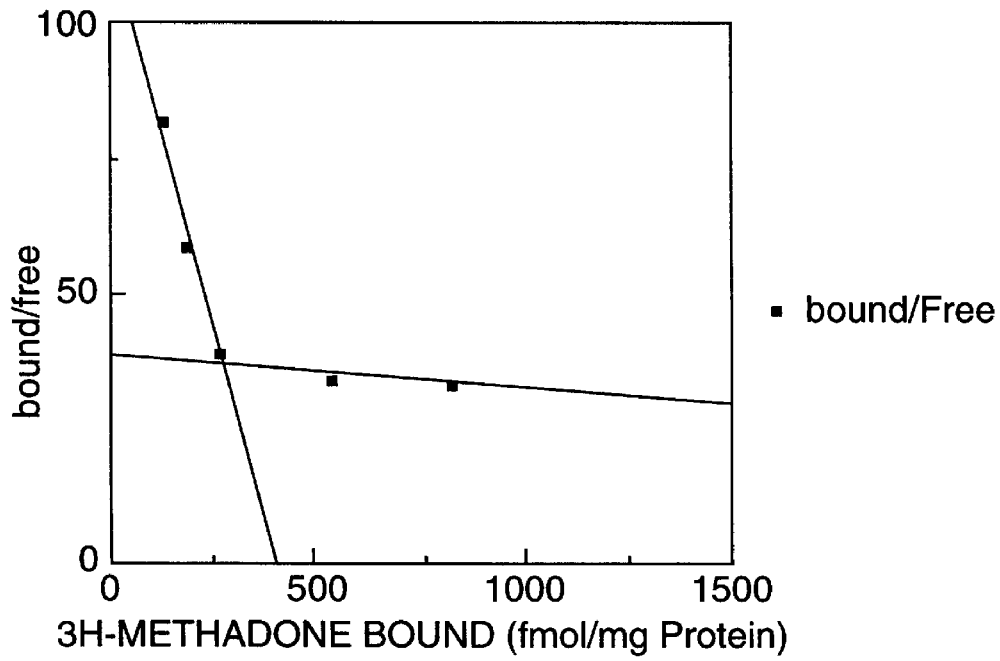

Surprisingly, however, specific binding was found using [$^3$H]-methadone. The results of Scatchard analysis of the methadone binding data are shown in FIG. 4.

For Scatchard analysis experiments, 0.25 ml aliquots of crude plasma membrane homogenate from transfected cell cultures was incubated in duplicate with increasing concentrations of [$^3$H]methadone (70.3 Ci/mmol; 10–3000 pM final concentration) under conditions described above. The estimated value for $B_{max}$ was derived from these data were obtained using the LIGAND computer program. Panel A of FIG. 4 shows the results of radiolabeled methadone binding with untransfected COS-7 cells; similar results were found with Ltk⁻ cell membranes. These results demonstrate no or negligible amounts of endogenous methadone binding by these cell membranes. Panel B shows the results using COS-7 cells transfected with the RcRSV-LC132 expression construct. The levels of specific binding shown in this graph correspond to a dissociation constant ($K_D$) of about $10^{-10}$ M for methadone and a $B_{max}$ of about 400–450 femtomoles/$\mu$g protein for the novel mammalian opioid receptor expressed by these cells.

Thus, the novel mammalian opioid receptor disclosed herein has the heretofore unknown property of exhibiting specific binding to the opiate analog, methadone, while showing no specific binding to a variety of other known opioid receptor agonists and antagonists. These results support the conclusion that the receptor disclosed herein is a completely novel and heretofore unsuspected member of the opioid receptor family, termed herein therefore MSOR.

EXAMPLE 4

Brain Tissue Distribution of MSOR Opioid Receptor Expression

The distribution of MRNA corresponding to expression of the MSOR receptor gene in various regions of the rat brain was determined by in situ hybridization of rat brain slices, as described in U.S. Ser. No. 08/149,093,now U.S. Pat. No. 5,658,783.

Results of these experiments are shown in FIG. 3. Panel A shows a section through the frontal cortex, preoptic area and caudate putamen; Panel B shows a section through the hypothalamus, thalamus and hippocampus; and Panel C shows a section through the pons and cerebellum. These experiments localized high level MSOR expression in the hypothalamus (arcuate (Arc), posterior (PH), lateral (LH) and ventromedial (VMH) hypothalamic nuclei, Panel B), certain nuclei of the thalamus (paraventricular thalamic nuclei (PVP), Panel B), the medial habenula (MHb, Panel B), the CA regions of the hypothalamus, the dentate gyrus (DG, Panel B), the locus coeruleus and certain cortical areas (medial preoptic are (MPA), Panel A and the cortex (Cx), Panel B). Virtually no signal was seen in the caudate putamen (Cpu, Panel A) or cerebellum (Cb, Panel C). Strong hybridization was also detected in sections of the brainstem (Panel C) and the spinal cord (not shown).

These results demonstrate that the MSOR receptor disclosed herein is expressed in rat brain in a variety of anatomically-distinct sites, suggesting an important role for this receptor in both higher brain function and central nervous system control of motor and sensory nerve signalling.

EXAMPLE 5

Identification of an Endogenously-occurring Peptide Ligand for the MSOR Opioid Receptor Due to the high level of sequence homology between the MSOR opioid receptor and the $\mu$-, $\delta$- and $\kappa$-opioid receptors found as disclosed in Example 2, it was appreciated that the novel receptor disclosed herein might specifically recognize an endogenous peptide ligand, and respond to binding such a ligand using a second messenger signalling system similar to those found associated with the previously-described opioid receptors. Since the MSOR opioid receptor had been found to be expressed in cells in the central nervous system in Example 4, and since MSOR opioid receptor MRNA is highly expressed in hypothalamus, porcine hypothalamic homogenates were screened for receptor binding activity. Inhibition of forskolin-stimulated, cyclic adenosine monophosphate (cAMP) accumulation in cells heterologously expressing the MSOR opioid receptor was used as an assay, which assay had been used to characterize the interaction of other opioid receptors and their ligands.

Acetic acid extracts of porcine hypothalamic tissues were prepared as follows. 4.5 kg of freshly frozen porcine hypothalamic tissue were extracted in 9 L of a solution of 0.5 M acetic acid/10 mM ascorbic acid/lmM EDTA. The extract was centrifuged to remove insoluble debris and the supernatant absorbed batchwise onto a $C_8$ silica matrix. Unbound material was removed by washing with water, and specifically-bound material was then eluted in a solution of 80% methanol. A total of 2 L of methanolic eluate were then concentrated by rotary evaporation to a final volume of 44 mL, and material having a molecular weight less than 10 kilodaltons was obtained by ultrafiltration using an Amicon Centriprep 10 column (Amicon, Beverly, Mass.). This material was applied in ten separate experiments to a cation exchange HPLC column (ProteinPak SP 8 HR, 10 ×100 mm, Waters) equilibrated with 10 mM $NH_4COO$. The column was developed with a linear gradient of $NH_4COO$ in 10% methanol at a flow rate of 1 mL/min; a total of 80 1 mL fractions were collected. 10% (100 $\mu$L) of each of 5 consecutive fractions were pooled and lyophilized, resulting in 16 pools. 5% of each pool was tested in duplicate for the capacity to inhibit forskolin-stimulated cAMP accumulation in cells heterologously expressing the MSOR opioid receptor.

Assays of ligand binding-associated inhibition of forskolin-stimulated cAMP accumulation in cells heterologously expressing the MSOR receptor were performed as follows. CHO cells, deficient in dihydrofolate reductase (dhfr⁻) were transfected with MSOR opioid receptor-encoding cDNA cloned into the expression vector pRcRSV (Invitrogen), as described in Example 3 above, using calcium phosphate co-precipitation (Okayama and Chen, ibid.). Stably-transfected clones were selected using G418, and screened for MSOR expression using a reverse transcriptase-PCR protocol (RT-PCR; Rappolee et al., 1988, Science 241: 1823–1825). One clone that tested positively for MSOR expression (LC-7) was used in ligand binding experiments.

For determination of cAMP levels, receptor-transfected CHO cells (i.e., LC-7) or untransfected CHO/dhfr⁻ cells, were plated in 24-well culture plates and grown to confluency. After removal of culture media, aliquots of HPLC fractions prepared as described above in a total volume of 0.2 mL DMEM containing 10 mM HEPES buffer, pH 7.4, 1 mM forskolin and 1 mM Ro 20–1724 (Rolipram, RBI) were added per well and cells incubated at 37° C. for 10 min. Cellular reactions were halted by the addition of 0.5 mL ice-cold ethanol, and plates were stored for 12 h or overnight at 80° C. Frozen plates were centrifuged and aliquots of the supernatant were removed and dried onto 96-well plates for cAMP determinations. cAMP determinations were performed using a commercially-available kit (Biotrak SPA, Amersham) essentially according to the manufacturer's instructions.

Figure 5:
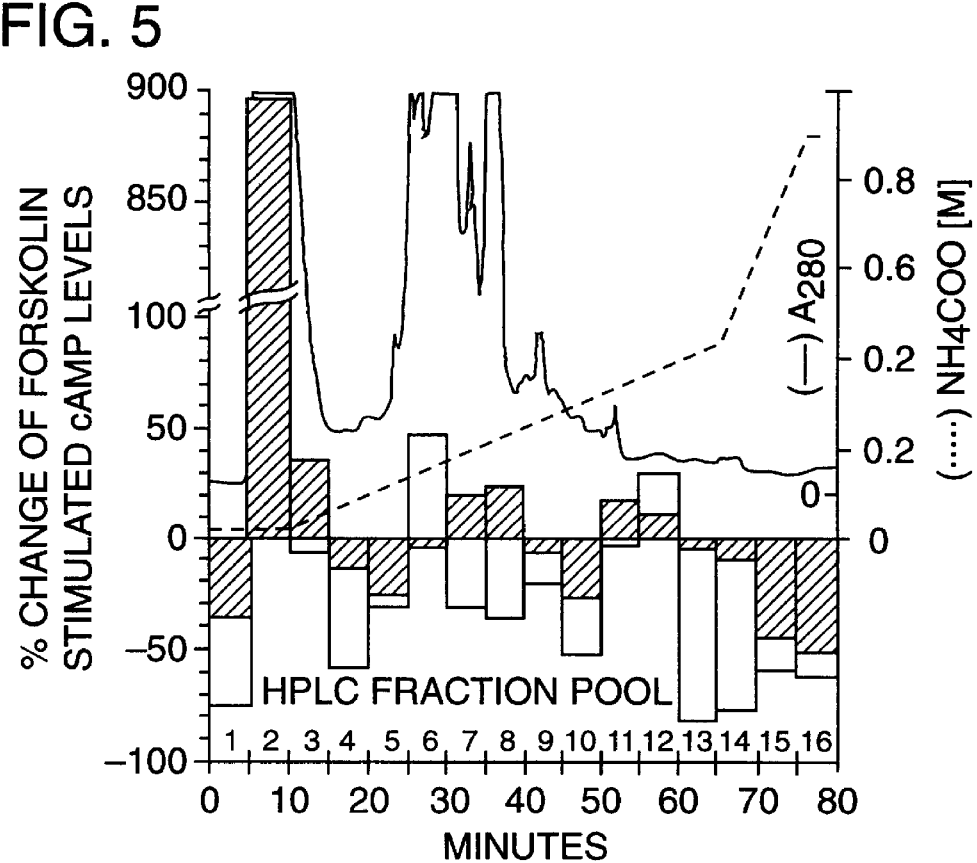
FIG. 5 shows the extent of inhibition of forskolin-stimulated cAMP accumulation in CHO cell heterologously expressing the MSOR of the invention by fractions of acetic acid-extracted peptides from porcine hypothalamus, wherein $A_{280}$ represents absorbance at 280 nm, shaded bars represent results obtained with untransfected CHO cells and open bars represent results obtained with MSOR transfected CHO cells.

The results of these experiments are shown in FIG. 5. Open bars represent results obtained with MSOR-expressing transfected CHO cells, and shaded bars represent results obtained with untransfected CHO cells. Pools 13 and 14 (corresponding to fractions 61–70 consistently showed adenyl cyclase inhibitory activity in transfected versus untransfected cells. The large increase in cAMP detected in fraction 2 is due to endogenous cAMP extracted from the tissue. Fractions 60–67 were found to contain most of the detected bioactivity, and were pooled for further purification by reverse-phase HPLC.

Figure 6:
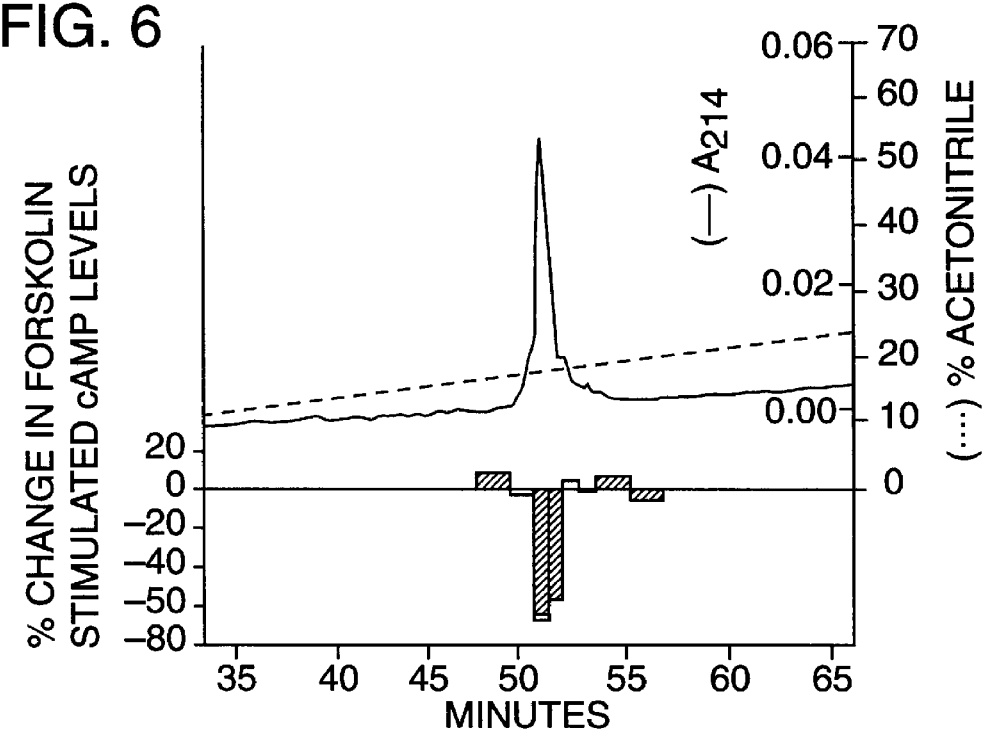
FIG. 6 shows the extent of inhibition of forskolin-stimulated cAMP accumulation in CHO cell heterologously expressing the MSOR of the invention by fractions of reverse-phase HPLC fractionated acetic acid-extracted peptides from porcine hypothalamus, wherein $A_{214}$ represents absorbance at 214 nm, and shaded bars represent results obtained with MSOR transfected CHO cells.

Reverse-phase HPLC was performed on pooled fractions 60–67 as follows. The complete bioactive material was loaded onto an octyl silica column (Superspher RP Select B, 2×125 mm, Merck) and eluted at a flow rate of 0.12 mL/min with a linear gradient of acetonitrile in 0.1% trifluoroacetic acid (TFA). Aliquots of fractions from this gradient were tested as described above, and the results of these assays shown in FIG. 6. Inhibition of forskolin-stimulated cAMP in MSOR-transfected CHO cells (shaded bars) was detected only in the major peak of eluted protein (measured as absorbance at 214 nm ($A_{214}$)).

The isolated material having adenyl cyclase inhibitory activity was analyzed by mass spectrometry and sequenced by Edman degradation. The material was determined to be a peptide having the sequence: Phe-Gly-Gly-Phe-Thr-Gly-Ala-Arg-Lys-Ser-Ala-Arg-Lys-Leu-Ala-Asn-Gln (SEQ ID No.:5). (Abbreviations for amino acids can be found in Zubay, *Biochemistry* 2d ed., 1988, MacMillan Publishing: New York, p. 33). Final yields of this peptide were about 200 picomoles from 4.5 kg hypothalamic tissue (wet weight). A computer database search revealed that this peptide had not been reported, either as a unique entity or as part of a larger protein. This peptide is designated orphanin FQ herein.

The primary structure of this novel peptide was compared with the primary structure of a number of other, naturally-occurring opioid peptides, as shown in FIG. 7. The amino terminal tetrapeptide sequence motif YGGF of the known opioid receptor ligands is strikingly similar to the amino terminal sequence FGGF found in orphanin FQ. Further, two clusters of basic amino acids found in the orphanin FQ peptide resemble the arrangement of positively-charged residues in Dynorphin A and β-Endorphin. However, none of these peptides could be shown to bind to the MSOR opioid receptor, suggesting a structural/functional divergence of the orphanin FQ peptide from these other opioid receptor ligands.

In order to verify that the isolated material had the observed properties of the pooled fraction from which it was isolated, a synthetic peptide having the deduced sequence was made and was found to be identical to the isolated peptide in its elution profile in reverse-phase HPLC assay and in molecular weight as determined by mass spectrometry. Moreover, the synthetic peptide was also found to inhibit adenyl cyclase production in forskolin-stimulated CHO cells transfected with and heterologously expressing the MSOR opioid receptor (shown in FIG. 7), having an $EC_{50}$ of 1.58 nM (±0.66 nM) and showing maximal inhibition (80%) at a concentration of about 100 nM. This high potency is comparable to that of other neuropeptides identified as the naturally-occurring ligands of other CNS-specific receptors. Thus, the isolated sequence, termed orphanin FQ herein, represents a novel endogenous peptide ligand for the MSOR opioid receptor.

To further characterize ligand binding of this novel ligand to the MSOR receptor, a series of peptide analogues were prepared that were tyrosine-substituted at different positions in the peptide sequence. cAMP inhibitions assays were performed using both the tyrosine-substituted peptides and monoiodotyrosine substituted peptides. Iodinated peptide was synthesized using the chloramine T method of Hunter and Greenwood (1962, Nature 194: 495). From these studies it was determined that the peptide analog having tyrosine at position 14 (Y-14; SEQ ID No.:6) and its monoiodo form (I-Y14) were MSOR agonists of almost equivalent potency to the orphanin FQ peptide, having $EC_{50}$ values of 1 nM and 3 nM, respectively.

Figure 8:
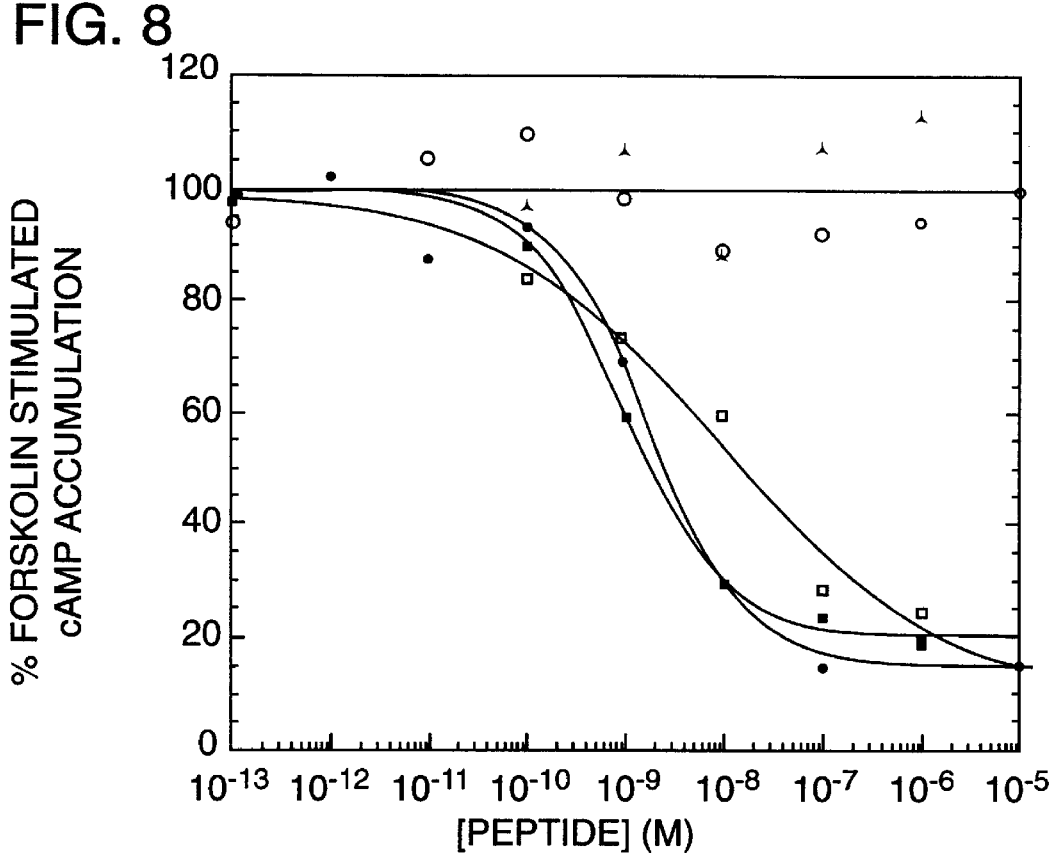
FIG. 8 is a graph illustrating the extent of inhibition of forskolin-stimulated cAMP accumulation in MSOR transfected CHO cells by the peptides orphanin FQ (filled circles); Y14-orphanin FQ (filled squares); monoiodinated Y14-orphanin FQ (open squares) and Leu-Enkephalin (open circles). Orphanin FQ-treated untransfected CHO cells are shown as filled triangles.

FIG. 8 shows a comparison of adenyl cyclase inhibitory activity of orphanin FQ (filled circles), Y14 orphanin FQ (filled squares), monoiodo Y14 orphanin FQ (open squares) and Leu- Enkephalin (open circles) in transfected CHO cells heterologously expressing the MSOR receptor; untransfected CHO cells were treated with orphanin FQ peptide as a control (filled triangles). Data were normalized so that cAMP levels in forskolin-stimulated, untransfected CHO cells was equal to 100%. cAMP levels were determined with all incubations being done at least twice in triplicate. FIG. 8 shows the results of a representative experiment.

The Y14 peptide was used to quantitatively assay receptor binding affinity for the novel ligand. Membranes from MSOR transfected CHO cells (LC-7) were used at a concentration of 55 μg membrane protein/assay. Membranes were incubated with increasing concentrations of ($^{125}$I)-Y14-orphanin FQ in a final volume of 0.2 mL binding buffer (50 mM HEPES, pH 7.4, 10 mM NaCl, 1 mM MgCl2, 2.5 mM CaCl2, 0.1% bovine serum albumin, 0.025% bacitracin) containing 1mg wheat germ agglutinin-coated SPA beads (Amersham). Iodinated peptide was synthesized as above using the chloramine T method. The monoiodinated species was obtained as a single peak, having a specific activity of 2200 Ci/mmole on the day of synthesis. Assays were performed in 96-well plates (OptiPlate, Caberra Packard), and the mixtures were incubated with shaking for 1 h. Bound ligand-associated radioactivity were determined by scintillation proximity (see, for example, Nelson, 1987, Anal. Biochem. 165: 287; Bosworth and Towers, 1989, Nature 341: 167) using a TopCount microplate scintillation counter (Canberra Packard). Concentrations of free ligand were calculated by subtracting the amount of specifically-bound ligand from the total amount of radioligand added.

Figure 9:
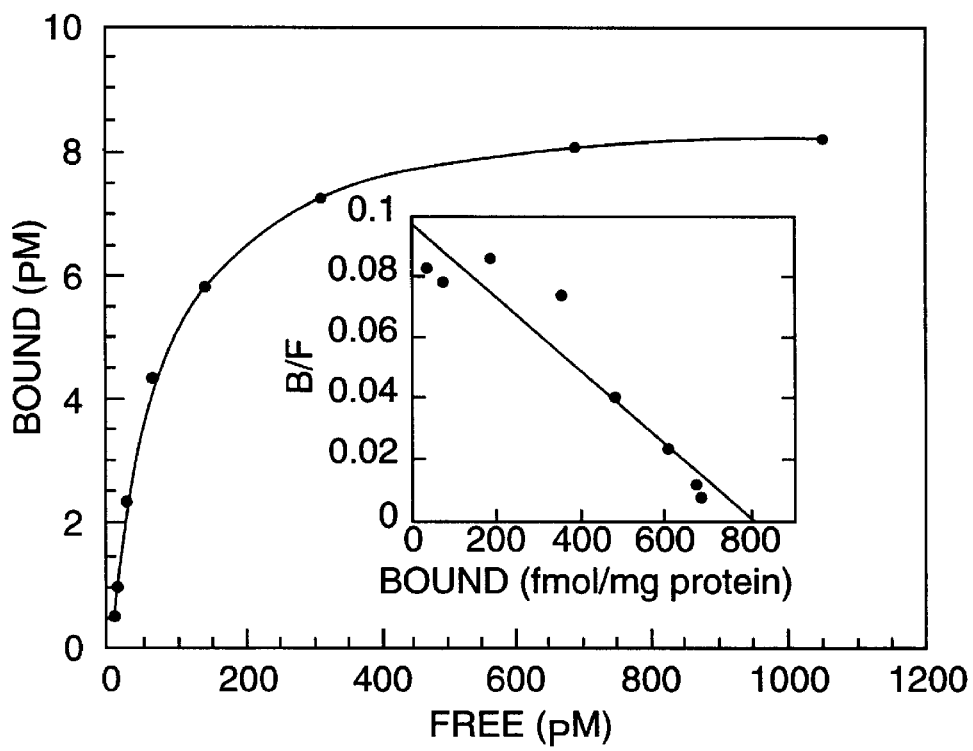
FIG. 9 is a graph of ($^{125}$I)-labeled Y14-orphanin FQ binding to isolated membranes from MSOR transfected CHO cells. The inset is a Scatchard analysis of these results.

The results of these experiments are shown in FIG. 9. The radiolabeled monoiodo-Y14-orphanin FQ peptide displayed saturable and displaceable binding to membranes of MSOR-expressing transfected cells, having a $K_d$ of 0.3 nM and a $B_{max}$ of 77.8 fmol/mg membrane protein. These experiments demonstrate that the novel. endogenous ligand peptide, orphanin FQ, and Y14-tyrosine substituted analogues thereof, bind saturably to the MSOR opioid receptor with high affinity, further confirming the conclusion that this peptide is a naturally-occurring, endogenous ligand for this receptor. These experiments also indicate that the Y14-substituted peptide can be used as a radioligand to detect and quantify MSOR opioid receptor levels.

EXAMPLE 6

Functional Characterization of the Orphanin FQ Peptide

In order to study the physiological activity of the orphanin FQ peptide, the in vivo activity of the peptide was investigated on unrestricted animals, and specifically, on nociception in such animals.

Figure 10A:
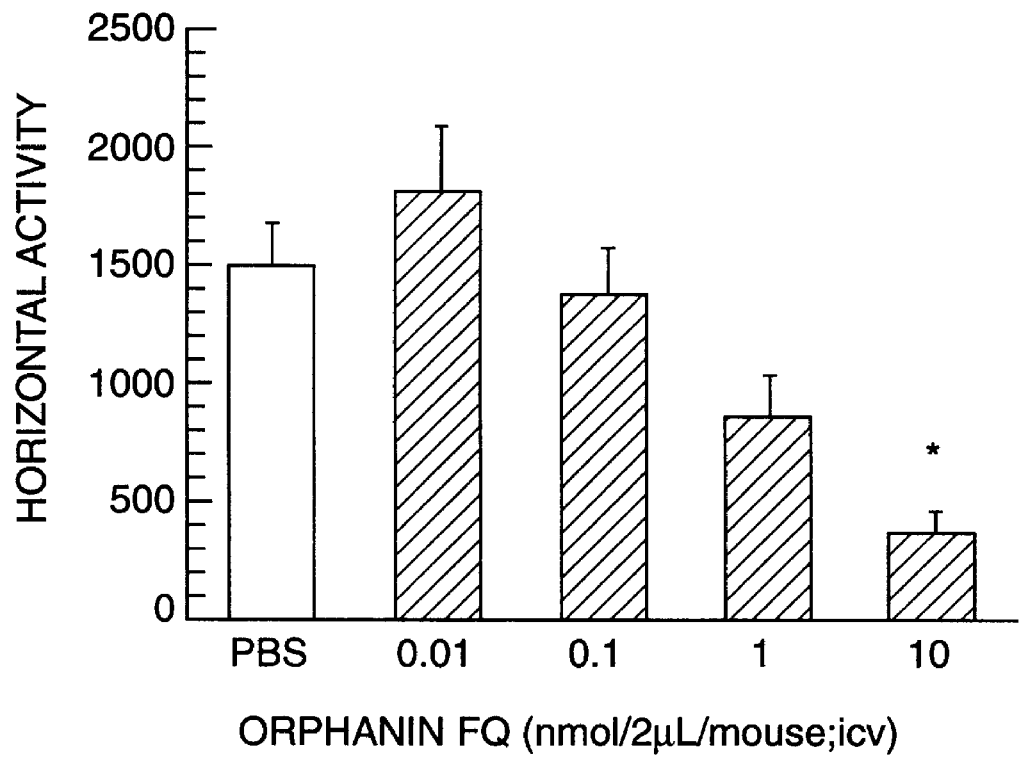
FIG. 10 shows the effects on horizontal activity (Panel A) and vertical activity (Panel B) in mice treated with varying concentrations of orphanin FQ peptide.
Figure 10B:
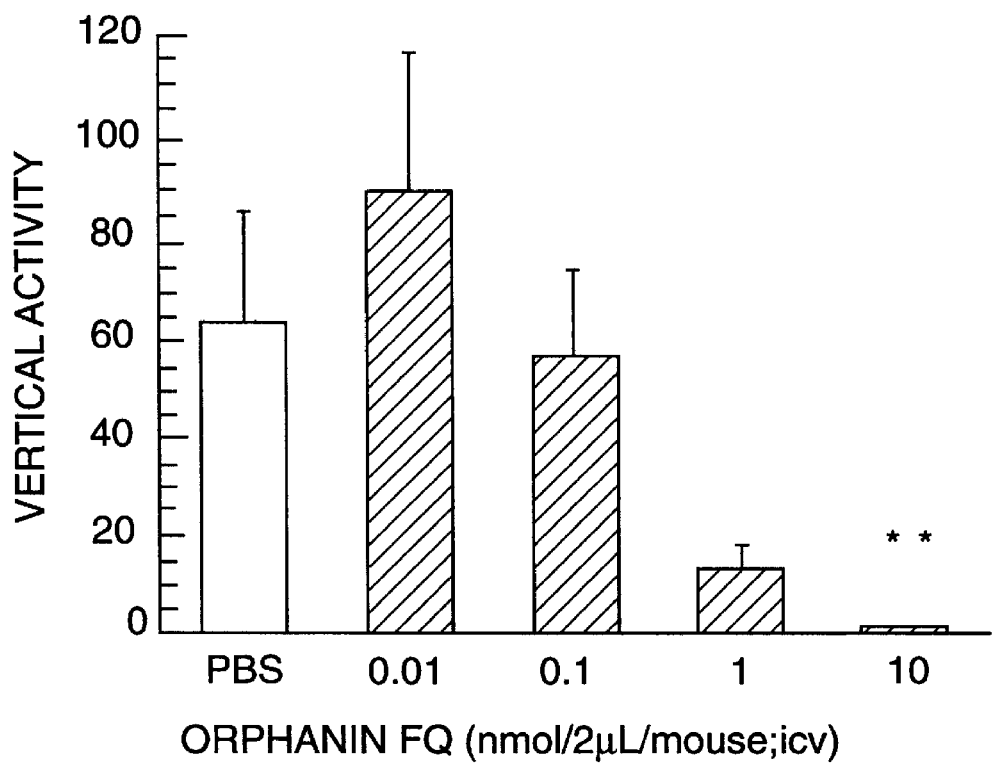

For these experiments, the peptide was administered intracerebroventricularly (i.c.v.) and intrathecally (i.t.) in mice. Immediately after peptide administration, mice were placed in transparent boxes in groups of three and behavioral signs recorded. Emphasis was placed on signs indicative of depressant, stimulant and autonomic effects of the peptide (as described by Irwin, 1968, Psychopharmacologia 13: 222). In open-field observation experiments, the peptide was noted to have a profound influence on locomotor activity, as well as a decrease in muscle tone, a loss of righting reflex, and ataxia. A quantitative investigation showed a decrease of .15 both horizontal and vertical locomotion following i.c.v. administration of the peptide at concentrations of 0.1–10 nmol/2 μL/mouse. These results are shown in FIG. 10. The effects of the peptide on horizontal and vertical locomotor activity was measured using Digiscan Animal Activity Monitors (Omnitech, Columbus, Ohio). The values for horizontal and vertical locomotor activity represent the total number of interruptions of the horizontal and vertical sensors during the first 10 min following administration of the peptide. Data are shown as the mean ± standard error of the mean.

Figure 11:
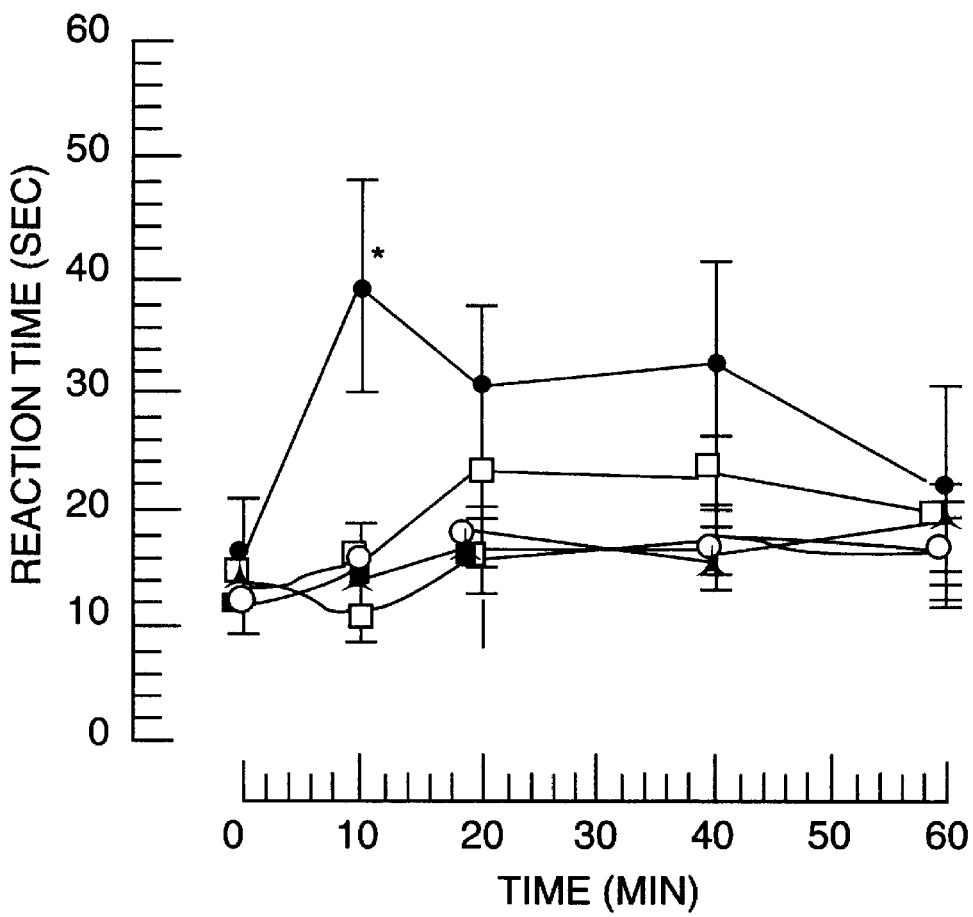
FIG. 11 illustrates the effects of orphanin FQ peptide on nociception in mice as determined using a hotplate assay.

On the other hand, the orphanin FQ peptide showed little analgesic effect in these mice, as recorded in a hot plate test, as shown in FIG. 11. Groups of 6–8 male MORO mice (weight=22g) were administered phosphate buffered saline (open circles) or varying doses of the orphanin peptide. Reaction time represents the time taken for the mice to lick their paws.

Figure 12:
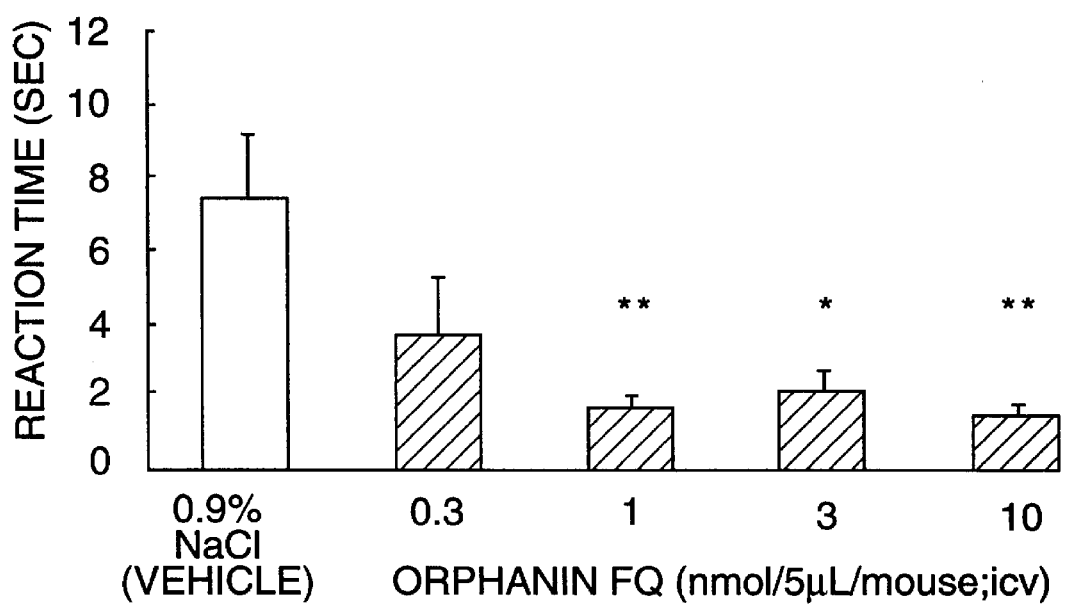
FIG. 12 shows the effects of orphanin FQ peptide on nociception in mice as determined using a tail-flick assay.

The hot plate was set to 58° C., and a cutoff time of 60 sec was used. No significant inhibition of nociception was detected, with the exception of mice administered the highest levels of peptide, 10 nmol/mouse, i.c.v. (designated by an asterisk). This observation was most likely related to a decrease in locomotor activity and muscle tone. At all doses tested, all animals exhibited normal toe- and tail-pinch reflexes, as shown in FIG. 12. No analgesic effect was observed when orphanin FQ was administered i.t. at 2.5–10 nmol/4 μL/animal; however, at the highest dose, hindlimb paralysis and decrease in locomotor activity was observed. No analgesic effect was observed in any mouse with this peptide at doses that did not produce significant decreases in motor activity and muscle tone. These results indicate that, despite structural homology with analgesia-producing opioid receptor ligands as described in Example 5, the orphanin FQ peptide appears to be pharmacologically distinct and to lack appreciable analgesic activity.

It should be understood that the foregoing disclosure emphasizes certain specific embodiments of the invention and that all modifications or alternatives equivalent thereto are within the spirit and scope of the invention as set forth in the appended claims.

TABLE I

|  | TMI | TMII | TMIII | TMIV | TMV | TMVI | TMVII | TM avg | avg/all |
|---|---|---|---|---|---|---|---|---|---|
| LC132[a] vs rat $\mu$[a] | 58[b] | 67 | 77 | 48 | 67 | 59 | 85 | 66 | 48 |
| LC132 vs rat $\kappa$[c] | 35 | 67 | 82 | 43 | 71 | 73 | 80 | 64 | 47 |
| LC132 vs mouse $\delta$[d] | 46 | 67 | 77 | 52 | 63 | 59 | 75 | 63 | 46 |
| rat $\kappa$ vs mouse $\delta$ | 62 | 83 | 91 | 57 | 75 | 64 | 90 | 75 | 52 |
| rat $\mu$ vs mouse $\delta$ | 69 | 90 | 86 | 48 | 83 | 77 | 85 | 77 | 51 |
| rat $\mu$ vs rat $\kappa$ | 54 | 80 | 91 | 33 | 75 | 73 | 95 | 72 | 49 |

[a]Bunzow et al.
[b]percent
[c]Minami et al. (1993) FEBS Letters 329, 291.
[d]Evans et al. (1992) Science 258, 1952.

---

What we claim is:

1. A purified peptide comprising the formula Phe-Gly-Gly-Phe-Thr-Gly-Ala-Arg-Lys-Ser-Ala-Arg-Lys-Leu-Ala-Asn-Gln (SEQ. ID No.5), wherein the amino acids are each individually in either the D or L stereochemical configuration, and the peptide binds to a receptor having an amino acid sequence identified as Seq. ID No. 4.

2. The peptide according to claim 1 that is radiolabeled with a radioactive isotope.

3. A purified peptide comprising the formula Phe-Gly-Gly-Phe-Thr-Gly-Ala-Arg-Lys-Ser-Ala-Arg-Lys-Tyr-Ala-Asn-Gln (SEQ. ID No. 6), wherein the amino acids are each individually in either the D or L stereochemical configuration, and the peptide binds to a receptor having an amino acid sequence identified as Seq. ID No. 4.

4. The peptide of claim 3 that is radiolabeled with a radioisotope of iodine.

* * * * *